(12) United States Patent
Weber et al.

(10) Patent No.: US 9,075,069 B2
(45) Date of Patent: Jul. 7, 2015

(54) MEASUREMENT OF AUTOANTIBODIES AT LOW CONDUCTIVITY WITH INCREASED SENSITIVITY

(71) Applicants: Baxter International Inc., Deerfield, IL (US); Baxter Healthcare S.A., Glattpark (CH)

(72) Inventors: Alfred Weber, Vienna (AT); Andrea Engelmaier, Vienna (AT); Hans-Peter Schwarz, Vienna (AT)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

(21) Appl. No.: 13/714,309

(22) Filed: Dec. 13, 2012

(65) Prior Publication Data

US 2013/0149700 A1 Jun. 13, 2013

Related U.S. Application Data

(60) Provisional application No. 61/570,211, filed on Dec. 13, 2011.

(51) Int. Cl.
G01N 33/564 (2006.01)
G01N 33/68 (2006.01)
G01N 33/543 (2006.01)

(52) U.S. Cl.
CPC ...... *G01N 33/6854* (2013.01); *G01N 33/54393* (2013.01); *G01N 33/564* (2013.01); *G01N 2333/4709* (2013.01)

(58) Field of Classification Search
None
See application file for complete search history.

(56) References Cited

U.S. PATENT DOCUMENTS

| 4,259,207 | A | | 3/1981 | Fruitstone et al. | |
|---|---|---|---|---|---|
| 5,183,735 | A | | 2/1993 | Lopez et al. | |
| 5,194,585 | A | * | 3/1993 | Paul et al. | 530/309 |
| 2012/0107957 | A1 | * | 5/2012 | Iizuka et al. | 436/501 |

FOREIGN PATENT DOCUMENTS

| EP | 0 064 275 A1 | 11/1982 |
|---|---|---|
| EP | 1 353 193 A1 | 10/2003 |
| WO | WO 2010/101213 A1 | 9/2010 |

OTHER PUBLICATIONS

Åkerström, B. et al., "A Physicochemical Study of Protein G, a Molecule with Unique Immunoglobulin G-binding Properties," *The Journal of Biological Chemistry*, Aug. 5, 1986, vol. 261, No. 22, pp. 10240-10247.

Baumketner, A. et al., "Amyloid β-protein monomer structure: A computational and experimental study," *Protein Science*, 2006, vol. 15, pp. 420-428.
Bernier-Valentin, F. et al., "Evidence for anti-tubulin autoantibodies in the form of immune complexes in human sera," *Clin. exp. Immunol.*, 1988, vol. 71, pp. 261-268.
Brettschneider, S. et al., "Decreased Serum Amyloid $\beta_{1-42}$ Autoantibody Levels in Alzheimer's Disease, Determined by a Newly Developed Immuno-Precipitation Assay with Radiolabeled Amyloid $\beta_{1-42}$, Peptide," *Biol Psychiatry*, 2005, vol. 57, pp. 813-816.
Djoumerska, I. et al., "The Autoreactivity of Therapeutic Intravenous Immunoglobulin (IVIg) Preparations Depends on the Fractionation Methods Used," *Scandinavian Journal of Immunology*, 2005, vol. 61, pp. 357-363.
Dobson. C.M. et al., "Experimental investigation of protein folding an misfolding," *Methods*, 2004, vol. 34, pp. 4-14.
Dodel, R.C. et al., "Intravenous immunoglobulins containing antibodies against β-amyloid for the treatment of Alzheimer's disease," *J Neurol Neurosurg Psychiatry*, 2004, vol. 75, pp. 1472-1474.
Hrncic, R. et al., "Antibody-Mediated Resolution of Light Chain-Associated Amyloid Deposits," *American Journal of Pathology*, Oct. 2000, vol. 157, No. 4, pp. 1239-1246.
Hughes, R. et al., "Anti-dsDNA antibodies: their role in the detection and monitoring of SLE," *CLI*, Nov. 2006, vol. 7, pp, 14-17.
Hyman, B.T. et al., "Autoantibodies to Amyloid-β and Alzheimer's Disease," *Ann Neurol*, 2001, vol. 49, pp. 808-810.
International Search Report mailed Apr. 9, 2013, for International Patent Application No. PCT/US2012/069587 6 pages.
Li, Q. et al., "Improvement of a low pH antigen-antibody dissociation procedure for ELISA measurement of circulating anti-Aβ antibodies," *BMC Neuroscience*, 2007, vol. 8, No. 22, 11 pages.
Makin, O.S. et al., "Molecular basis for amyloid fibril formation and stability," *PNAS*, Jan. 11, 2005, vol. 102, No. 2, pp. 315-320.
Moir, R.D. et al., "Autoantibodies to Redox-rnodified Oligomeric Aβ are Attenuated in the Plasma of Alzheimer's Disease Patients," *The Journal of Biological Chemistry*, Apr. 29, 2005, vol. 280, No. 17, pp. 17458-17463.
Mruthinti, S. et al., "Autoimmunity in Alzheimer's disease: increased levels of circulating IgGs binding Aβ and RAGE peptides," *Neurobiology of Aging*, 2004, vol. 25, pp. 1023-1032.
Nath, A. et al., "Autoantibodies to Amyloid β-Peptide (Aβ) are Increased in Alzheimer's Disease Patients and Aβ Antibodies Can Enhance Aβ Neurotoxicity," *NeuroMolecular Medicine*, 2003, vol. 3, pp. 29-39.
O'Nuallain, B. et al., "Conformational Abs recognizing a generic amyloid fibril epitope," *PNAS*, Feb. 5, 2002, vol. 99, No. 3, pp. 1485-1490.

(Continued)

*Primary Examiner* — Jacob Cheu
(74) *Attorney, Agent, or Firm* — Morgan, Lewis & Bockius LLP

(57) ABSTRACT

Methods for detecting or capturing low-avidity autoantibodies in a biological sample are provided. Target antigen used to assay for the low-avidity autoantibodies of interest is immobilized on a solid phase. The biological sample is contacted under low conductivity condition with the target antigen for which the autoantibodies has specific binding affinity. Binding of the target antigen to the autoantibodies of interest in the biological sample is then detected to ascertain the presence or concentration of the autoantibodies of interest.

26 Claims, 9 Drawing Sheets

(56) References Cited

OTHER PUBLICATIONS

O'Nuallain, B. et al., "Diagnostic and Therapeutic Potential of Amyloid-Reactive IgG Antibodies Contained in Human Sera," *The Journal of Immunology*, 2006, vol. 176, pp. 7071-7078.

O'Nuallain, B. et al., "Human Plasma Contains Cross-Reactive Aβ Conformer-Specific IgG Antibodies," *Biochemistry*, 2008, vol. 47, pp. 12254-12256.

O'Nuallain, B. et al., "Anti-amyloidogenic Activity of IgGs Contained in Normal Plasma," *J Clin Immunol*, 2010, vol. 30(Suppl 1), pp. S37-S42.

Relkin, N.A. et al., "IVIG Contains Antibodies Against Oligomers and Fibrils of Beta Amyloid," *Alzheimer's and Dementia*, 2008, vol. 3, p. S196, Abstract No. 02-05-05.

Serpell, L.C., "Alzheimer's amyloid fibrils: structure and assembly," *Biochimica et Biophysica Acta*, 2000, vol. 1502, pp, 16-30.

Sherer, Y. et al., "Intravenous Immunoglobulin (IVIg) in Autoimmune Diseases—Expanding Indications and Increasing Specificity," Research Report of the American Autoimmune Related Diseases Association, Inc., Sep. 2000, pp. 85-91.

Sohn, J-H. et al., "Dentification of autoantibody against beta-amyloid peptide in the serum of elderly," *Frontiers in Bioscience*, Jan. 1, 2009, vol. 14, pp. 3879-3883.

Solomon, B. et al., "Monoclonal antibodies inhibit in vitro fibrillar aggregation of the Alzheimer's β-amyloid peptide," *Proc. Natl. Acad. Sci. USA*, Jan. 1996, vol. 93, pp. 452-455.

Szabo, P. et al., "Natural human antibodies to amyloid beta peptide," *Autoimmunity Reviews*, 2008, vol. 7, pp. 415-420.

Szabo, P. et al., "Measurement of Anti-Beta Amyloid Antibodies in Human Blood," *J. Neuroimmunol.*, Oct. 8, 2010, vol. 227, No. 1-2, pp. 167-174.

Taguchi, H. et al., "Autoantibody-catalyzed Hydrolysis of Amyloid β Peptide," *The Journal of Biological Chemistry*, Feb. 22, 2008, vol. 283, No. 8, pp. 4714-4722.

Weber, A. et al., "Biochemical, molecular and preclinical characterization of a double-virus-reduced human butyrylcholinesterase preparation designed for clinical use," *Vox Sanguinis*, 2011, vol. 100, pp. 286-297.

Weksler, M.E. et al., "Patients with Alzheimer's disease have lower levels of serum anti-amyloid peptide antibodies than healthy elderly individuals," *Experimental Gerontology*, 2002, vol. 37, pp. 943-948.

Wild, D. ed., The Immunoassay Handbook, 1994, Stockton Press, New York, NY, Table of Contents.

\* cited by examiner

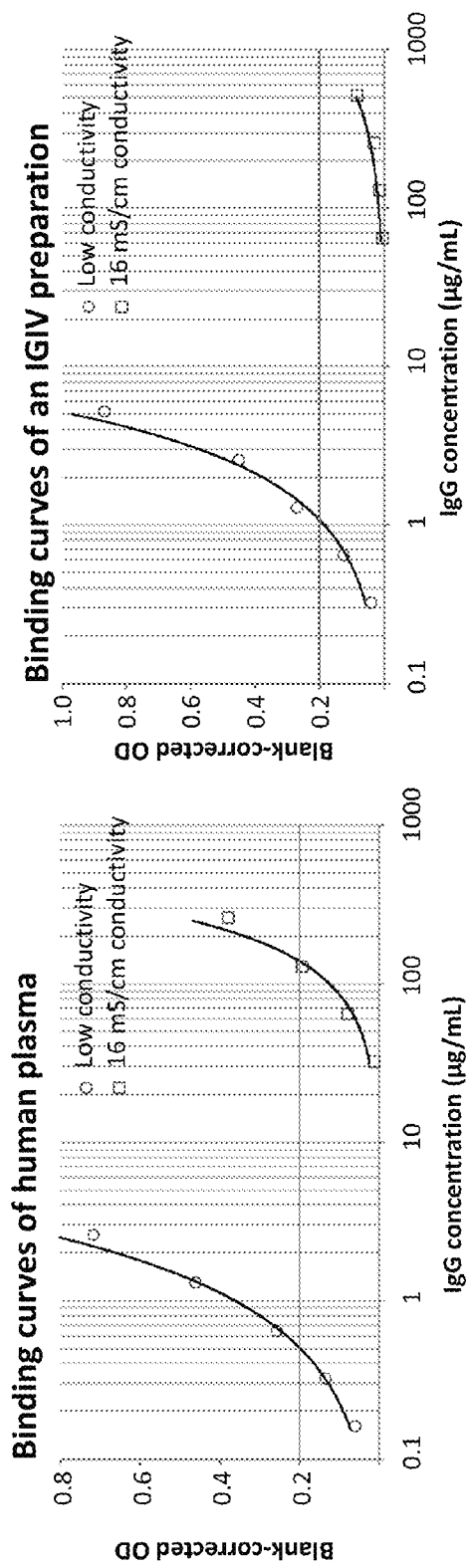
Figure 1. Measurement of anti-Aβ40 IgG in plasma and intravenous IgG

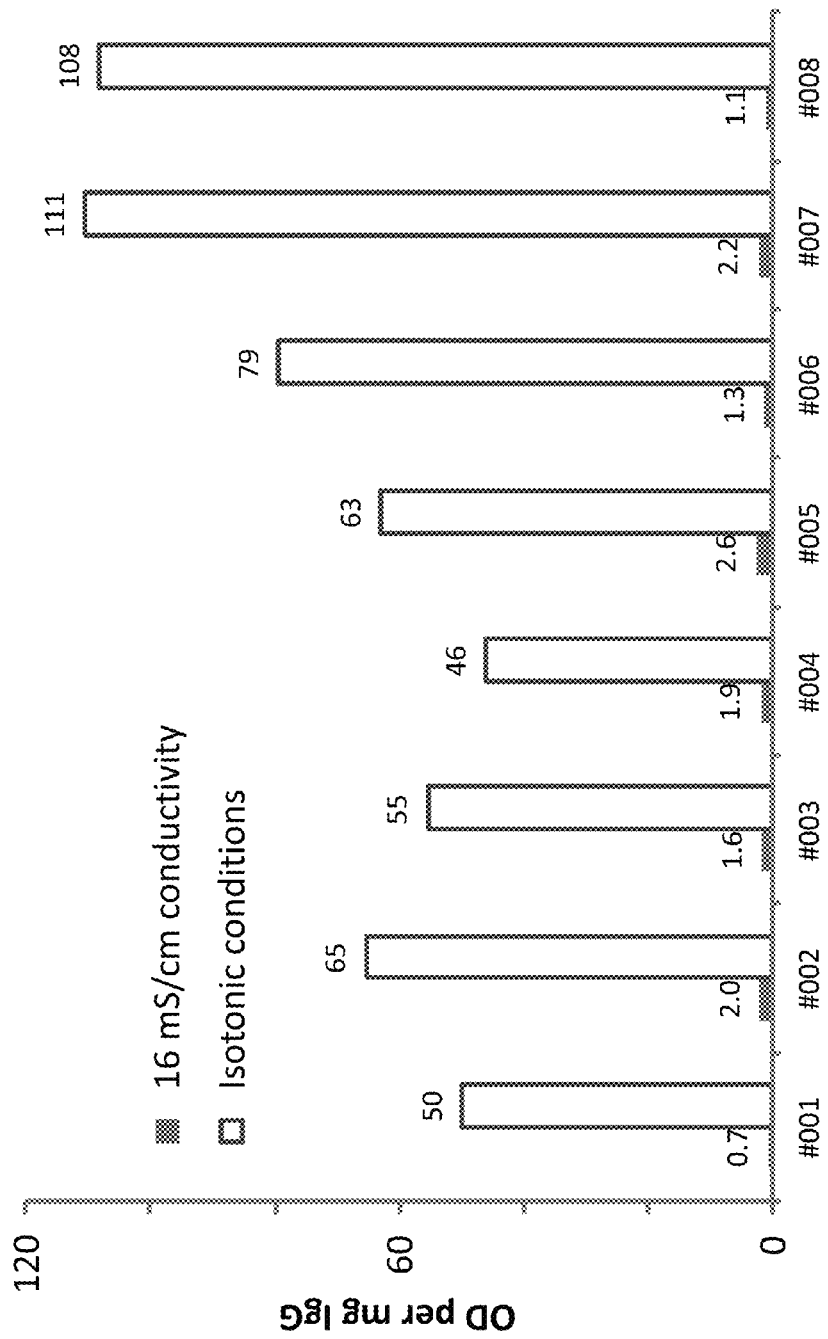

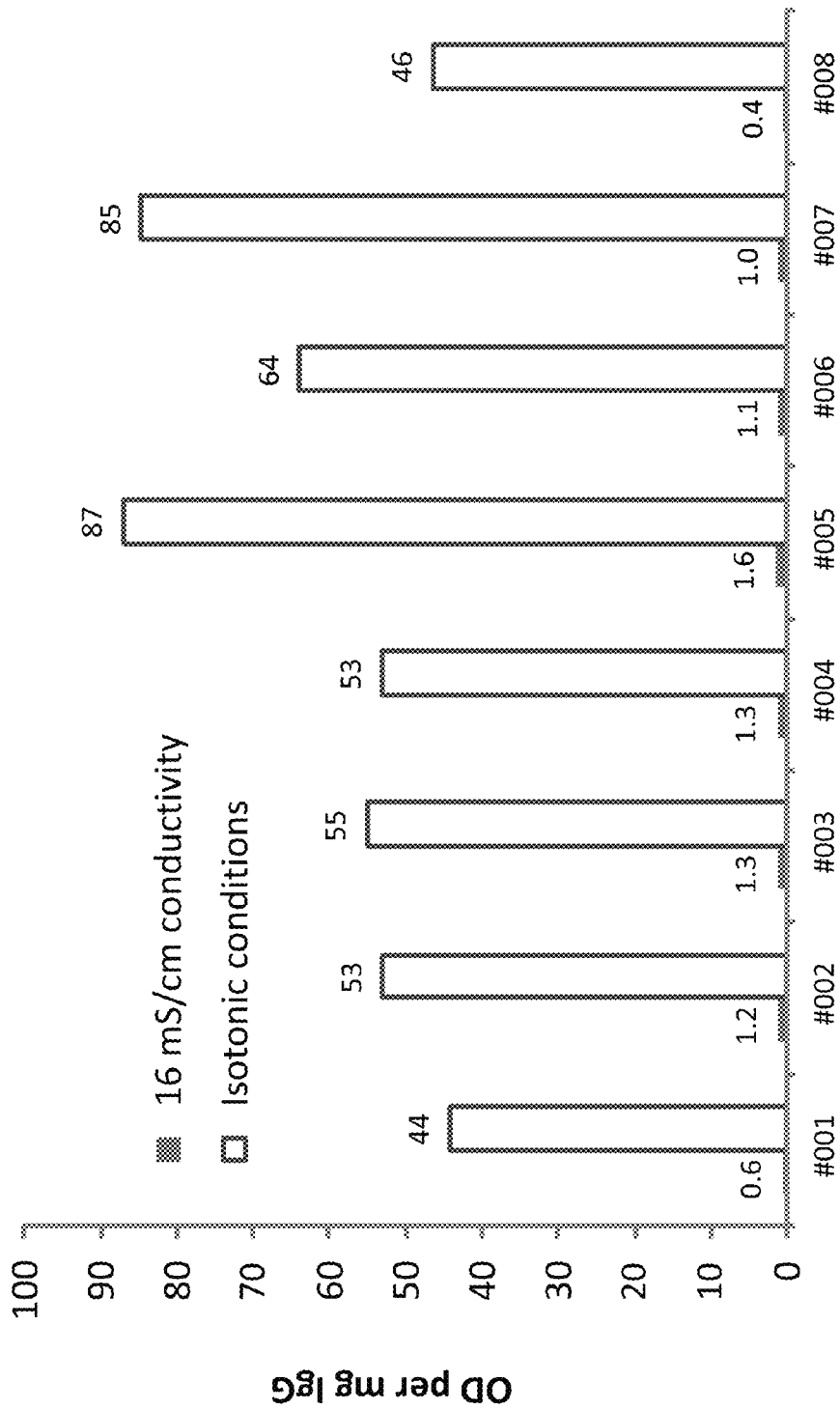

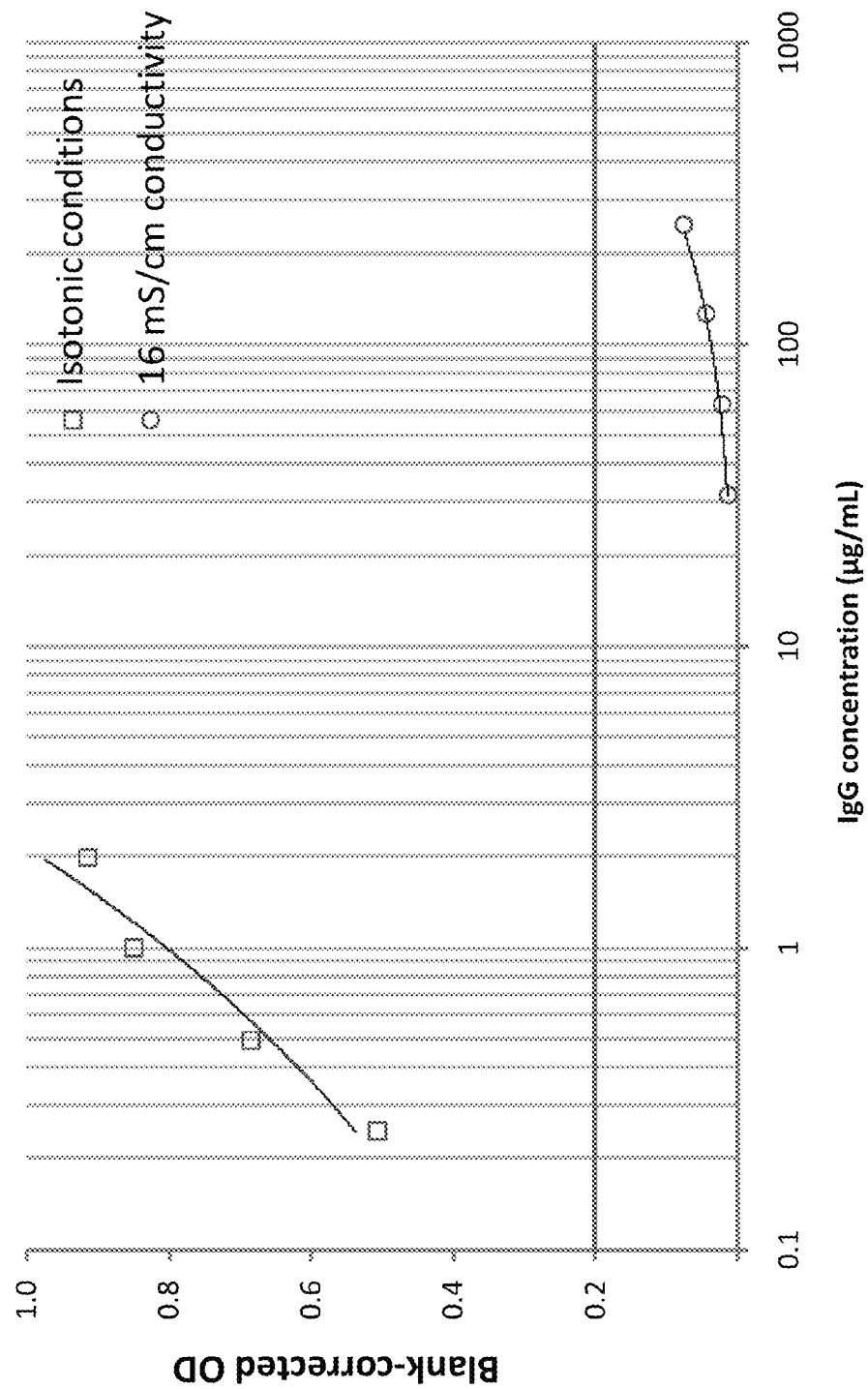

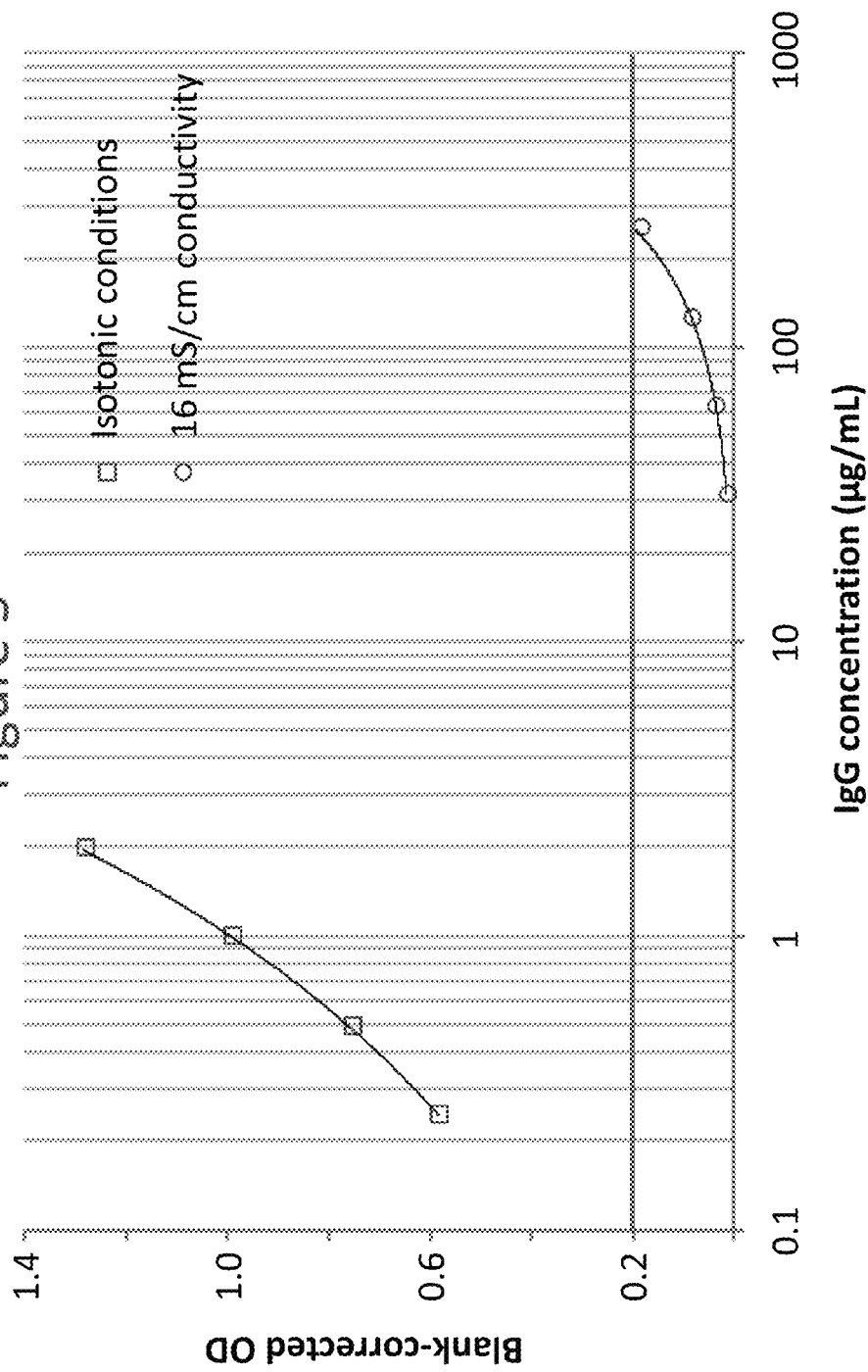

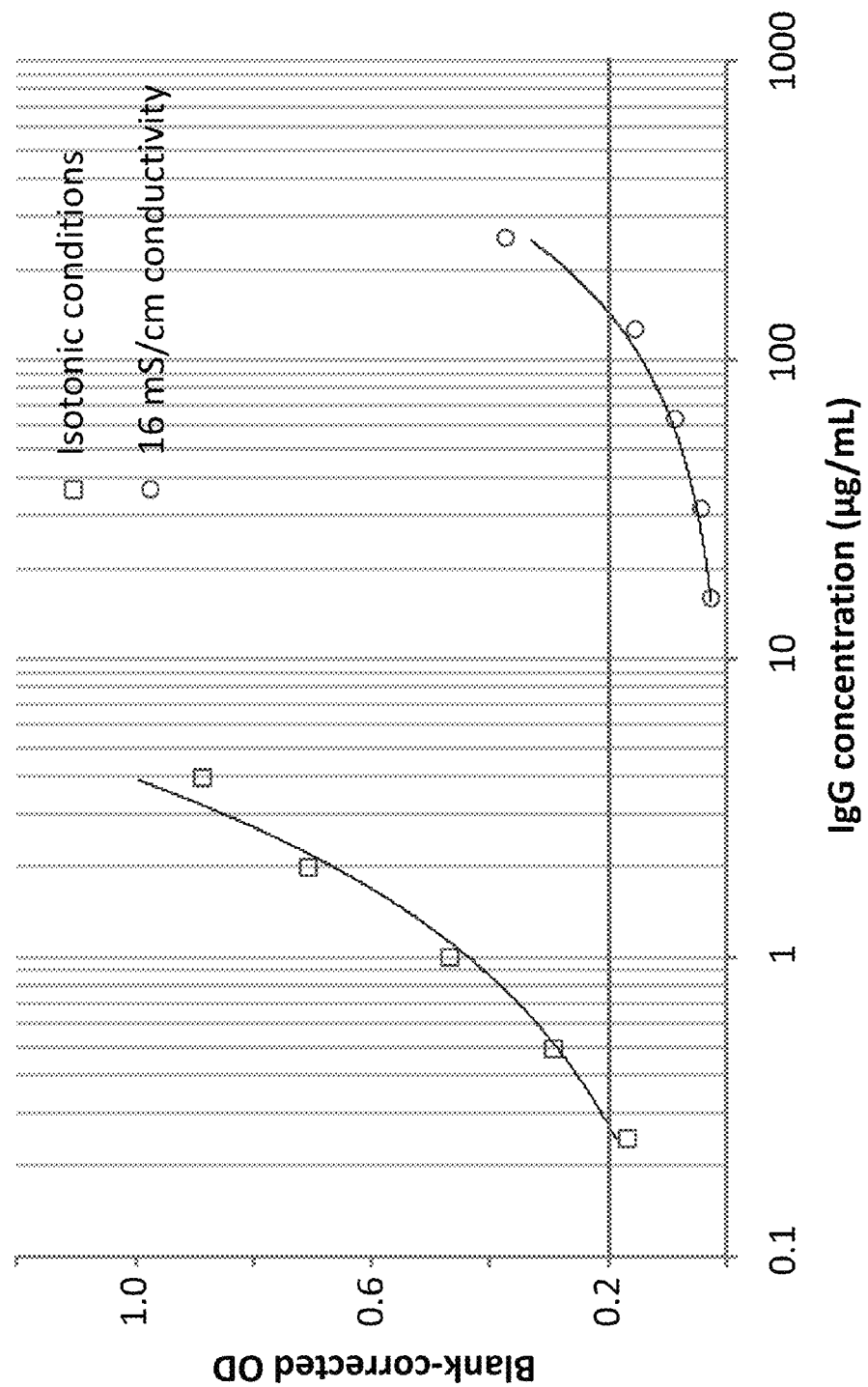

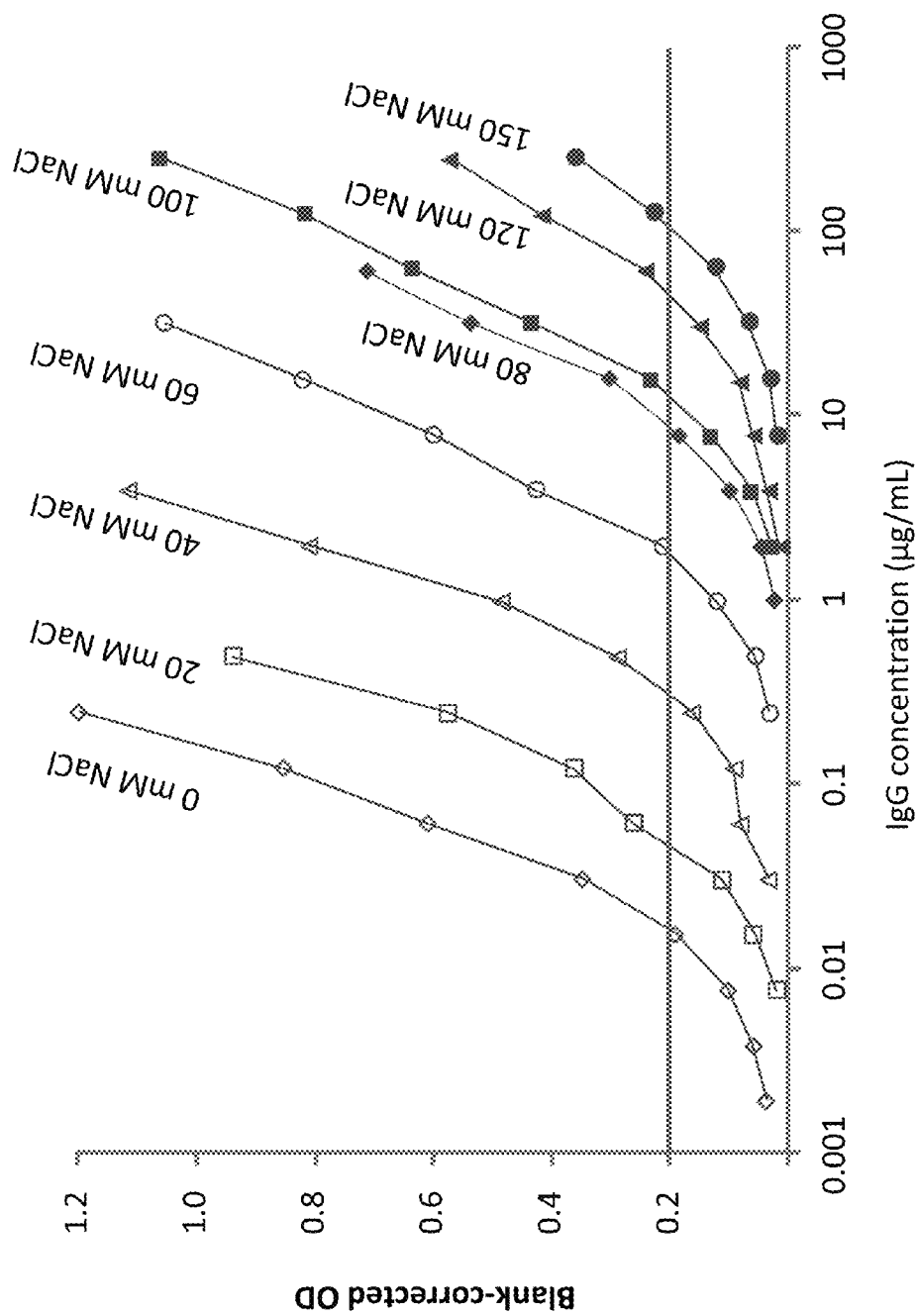

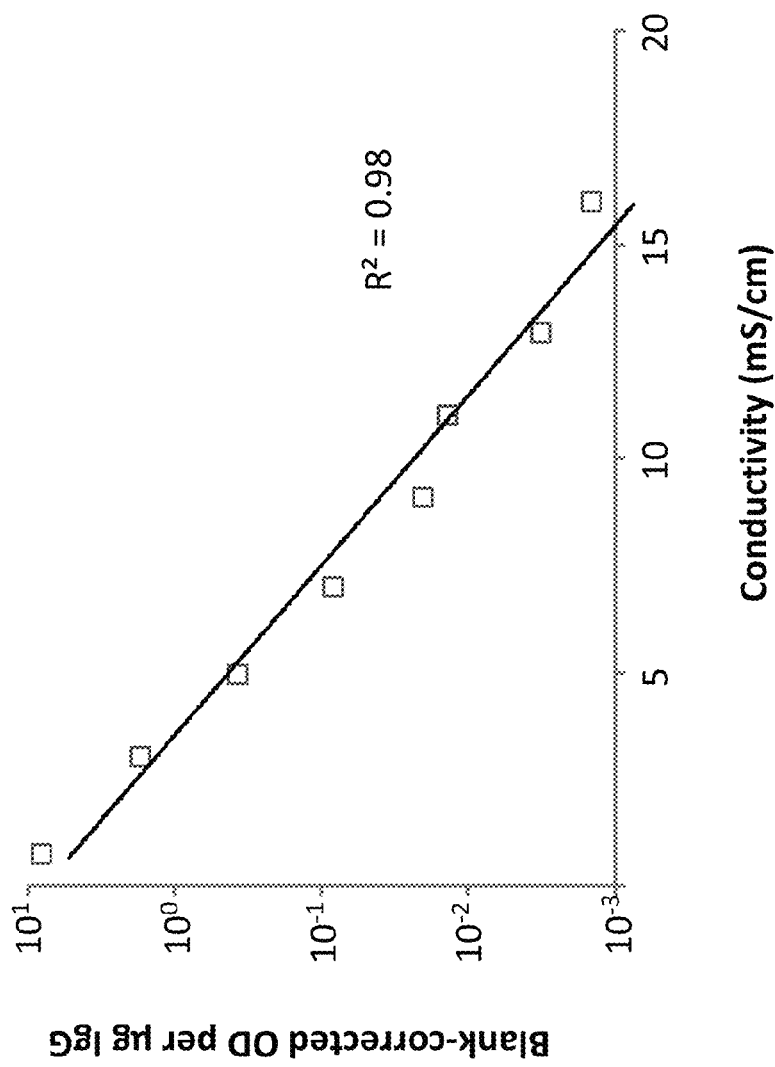

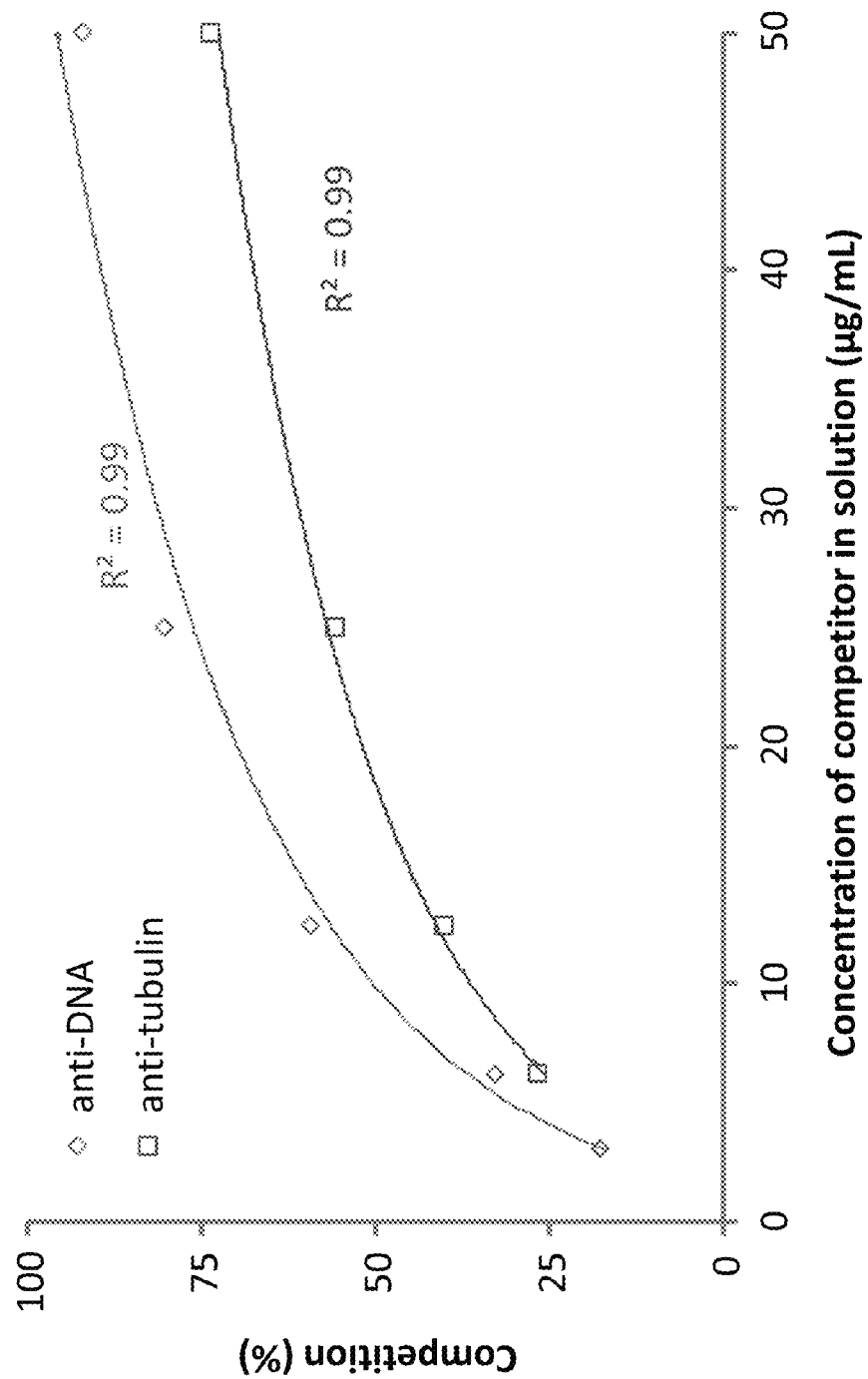

MEASUREMENT OF AUTOANTIBODIES AT LOW CONDUCTIVITY WITH INCREASED SENSITIVITY

The present application claims the benefit of U.S. Provisional Application No. 61/570,211, filed Dec. 13, 2011, which is expressly incorporated herein by reference in its entirety for all purposes.

BACKGROUND OF THE INVENTION

The role of autoantibodies in diseases is a subject of intense research. Autoantibodies form a diverse repertoire with the capacity to target antibody, peptidic, or nucleic acid self-antigens. These autoantibodies may be monovalent or polyreactive and may exhibit varying affinities and avidities; dissociation constants can range from $10^{-5}$ to $10^{-8}$ M. While autoantibodies are widely implicated in autoimmune diseases, a subset of autoantibodies also plays a non-pathological role in maintaining immunological homeostasis and a properly functioning immune system. There is mounting evidence that autoantibodies are essential to the survival and/or development of T and B lymphocytes in the peripheral immune system, defense against microbial infections, inflammation suppression, mediation of efferocytosis, anti-idiotypic immunomodulation, and regulation of cytokine production. See, Elkon et al. (2008) *Nat Clin Pract Rheumatol* 4(9): 491-498; Silverman et al. (2009) *Discovery Medicine* 8(42): 151-156; and Lacroix-Desmazes S. et al., (1998): *J Immunol Methods* 216, 117-137.

Detection of autoantibodies in patients suspected of having, or diagnosed with, an autoimmune disease has significant utility in research or in the clinical context. Autoantibodies can serve as a diagnostic marker or indicator of disease progression. For instance, rising levels of dsDNA antibodies in SLE (systemic lupus erythematosus) correlate with increasing disease activity and sometimes precede clinical relapse in patients. Numerous autoantibodies have been linked in the literature to various disorders. See, Watts et al. (2002) Medicine 30(10): 2-6. Some examples include anti-amyloid-β in Alzheimer's disease; anti-thyroglobulin in thyroiditis; anti-tubulin in autoimmune liver disorders, autoimmune hearing loss, and autoimmune thyroid diseases; rheumatoid factors in rheumatoid arthritis; and anti-dsDNA antibody (Ab) in SLE.

Measurement of autoantibodies is also useful for therapeutic purposes, especially with the advent of intravenous immunoglobulin (IVIG) therapy for an increasing number of autoimmune diseases. Examples include, without exclusion, immune thrombocytopenic purpura, Kawasaki disease, Guillain-Barre syndrome, polymyositis/dermatomyositis, vasculitis and systemic lupus erythematosus (SLE). See, Yaniv et al. (September 2000) "Intravenous Immunoglobulin (IVIG) in Autoimmune Diseases Expanding Indications and Increasing Specificity" Research Report of the American Autoimmune Related Diseases Association, Inc. IVIG therapy has also been shown to be effective in the treatment of Alzheimer's disease. Studies have demonstrated anti-Aβ autoantibodies' role in facilitating the clearance of neurotoxic Aβ assemblies and decreasing the serum Aβ in CSF (cerebrospinal fluid), which in turn reduce cerebral Aβ peptide deposition and cognitive decline. See, Szabo et al. (2008) *Autoimmuity Reviews* 7: 415-420.

Results from an autoantibody assay, however, are only as useful as the quality of the data it produces. Conventional immunodetection methods such as the Farr assay, *Crithidia* IFA (immunofluorescent assays) and ELISA compromise between specificity and sensitivity and have their respective constraints. See, Hughes et al. (2006) CLI 18(7):12-17. Farr assays, for instance, precipitate immune complexes of dsDNA/anti-dsDNA Abs at high salt concentrations in ammonium sulphate, which causes low avidity dsDNA/anti-dsDNA antibody complexes to dissociate and thereby limits detection to autoantibodies with relatively high avidity. This result is a setback as autoantibodies are highly heterogeneous with respect to their avidity and those of moderate to low avidity may also have clinical significance, as seen in Alzheimer's disease (AD) where IgG autoantibodies bind to epitope on beta amyloid (Aβ) monomers and aggregate with moderate avidity. See, Szabo et al. (2010) Journal of Neuroimmunology 227: 167-174. Furthermore, Farr assays employ a radiolabel and are both labor-intensive and expensive. IFA *Crithidia*, while capable of detecting autoantibodies of moderate to high avidity, is fairly time-consuming and subjective due to its dependence on slide scoring. ELISA assays are generally more sensitive and susceptible to automation and, thus, often the assay of choice.

Standard ELISA methods are not without shortcomings. They are generally less specific than other methods such as immunopreciptation and immunoelectrophoresis and suffer from a host of issues as documented in the literature. As a case in point, standard ELISA methods have yielded widely disparate estimates on the relative titers of anti-Aβ autoantibodies in AD patients versus aged normal controls. Initial studies of intact plasma specimens by standard ELISA methods ascribed lower titers of endogenous antibodies against Aβ monomers to AD patients than aged-matched non-demented controls (Weksler et al., *Exp Gerontol.*, 37:943-948 (2002)). Subsequent studies reported equal or increased titers of circulating anti-Aβ monomers antibodies in AD patients (Mruthinti et al., *Neurobiol Aging*, 25:1023-1032 (2004)) based on ELISAs performed on plasma immunoglobulin eluted from Protein G columns at low pH (Akerström et al., *J Biol. Chem.*, 261:10240-10247 (1986)). The higher titers obtained by this method were hypothesized to reflect the presence of a pool of bound anti-amyloid antibodies that were undetected in assays of whole plasma and measurable when freed from antigen by acidification in the course of protein G purification.

Misfolding and aggregation of the Aβ is central to the pathogenesis of AD. The human immunoglobulin G (IgG) repertoire contains autoantibodies against the Aβ peptide that arise in the absence of vaccination or passive immunization and such anti-Aβ autoantibody activity has been detected in the blood of normal adults of various ages and patients with AD (Weksler et al., Exp Gerontol., 37:943-948 (2002); Hyman et al., Ann Neurol., 49:808-810.5 (2001); Mruthinti et al., Neurobiol Aging., 25:1023-1032 (2004); Nath et al., Neuromolecular Med., 3:29-39 (2003); Sohn et al., Frontiers in Bioscience., 14:3879-3883 (2009)). The interest in such anti-amyloid-β autoantibodies has intensified with the discovery that human IVIG containing elevated levels of the autoantibodies have therapeutic effect in AD patients (Dodel et al., J Neurol Neurosurg Psychiatry., 75:1472-1474 (2004); Hyman et al., Ann Neurol., 49:808-810.5 (2001); Mruthinti et al., Neurobiol Aging., 25:1023-1032 (2004)).

Despite recent advances in Alzheimer's research, efforts to accurately measure anti-amyloid-β autoantibodies have been undermined by many obstacles. One obstacle is the existence of multiple classes of human antibodies that recognize linear as well as conformational neo-epitopes on aggregated forms of Aβ. Reports to date have identified endogenous human antibodies against Aβ fibrils (O'Nuallain et al., *J. Immunol.*, 176:7071-7078 (2006)), Aβ oligomers (Moir et al., *J Biol. Chem.*, 280:17458-17463 (2005); Relkin et al., *Alzheimer's*

*and Dementia*, 3:S196, X (2008); O'Nuallain et al., Biochemistry, 47:12254-12256 (2008)) and conformational epitopes on Aβ monomers (Baumketner A et al., *Prot Sci.*, 15:420-428 (2006)). Other types of amyloid binding antibodies and even catalytic antibodies against Aβ have been reported (Taguchi H et al., *J Biol. Chem.*, 284:4714-4722 (2008)).

The measurement of low-avidity, polyreactive autoantibodies is a particular challenge due to high background binding to empty ELISA wells and assay interference from other plasma proteins and components in the blood samples. See, Szabo et al. (2010) Journal of Neuroimmunology 227:167-174. These problems must be overcome as a large proportion of IgG autoantibodies in IVIG are polyreactive and low-avidity.

Efforts to improve the sensitivity and signal-to-noise ratio of anti-Aβ autoantibody assays have been made, including a radio-immunoprecipitation assay developed by the Brettschneider research team. See, Brettschneider et al. (2005) Biol. Psychiatry 57: 813-816. In another study, pre-assay passage of IVIG over polystyrene and/or agarose columns was done in the hopes of depleting non-specific autoantibody binders. Results were less than ideal as the depletion was not specific to autoantibodies which bind blank plates and depletion reduced the already low concentrations of anti-Aβ autoantibodies, which further complicated measurement. The low-avidity of polyreactive autoantibodies makes them difficult to detect, and the resulting signal intensity is further affected by interference from other plasma proteins and components, leading to underestimates of the anti-amyloid activity.

A common practice to compensate for low autoantibody concentrations, which are common for polyreactive, low-avidity anti-amyloid-β autoantibodies, employs less diluted samples for assay. This technique, however, increases both signal strength and noise. Another approach involves treatment of bound autoantibody-antigen complexes with chaotropic salt (ammonium thiocyanate). See, Szabo et al. (2010) Journal of neuroimmunology 227:167-174.

At the other end of the spectrum, recent methods directed at improving signal strength of the low-avidity, polyreactive autoantibody detection have resulted in over-estimates of anti-amyloid activity. For example, a technique that had shown promise involves the isolation of IgG from human plasma via protein G chromatography and acid elution; the assays resulted in a 50-fold increase in apparent anti-Aβ antibody titers (Li et al., BMC Neurosci., 8:22 (2007)). The high titers were, however, attributed to partial denaturation and artificially induced polyvalency of antibodies in the sample, as evidenced by a 100-fold increase in blank plate binding.

To explain, polyreactive antibodies to both foreign and self-antigens are part of the natural antibody repertoire of humans (Djoumerska et al., *Scand J of Immunol.*, 61: 357-363 (2005)). Most polyreactive antibodies have germ line hypervariable regions, belong to the IgG isotype, display lower affinity and avidity for their antigens as compared to monovalent affinity-maturated antibodies, and have more flexible antigen-binding sites. They are thought to serve as a defense mechanism against pathogens.

The accurate measurement of autoantibodies is key to advancing research in the pathogenesis of Alzheimer's disease and other autoimmune diseases. Likewise, clinical assessment and treatment of patients suspected of or diagnosed with autoimmune disease demand improved assays for autoantibodies. With the discovered potential of IVIG as an Alzheimer's treatment comes an intensified need to overcome some of the impediments to anti-amyloid autoantibody measurement and permit the development of a standard for therapeutic use and further studies. Reliable assays for low-avidity, polyreactive autoantibodies have largely proven elusive. As such, there is a need to develop improved assays for low-avidity, polyreactive anti-amyloid autoantibodies with both sensitivity and specificity. The present invention provides autoantibody assays at low conductivity conditions which increase signal strength without negatively impacting binding selectivity.

SUMMARY OF THE INVENTION

The present invention provides a low conductivity buffer system and methods of using same to achieve autoantibody detection with enhanced sensitivity. The increased sensitivity permits detection of autoantibodies even at concentrations as low as 0.2 µg/mL, thereby placing less constraints on the detection threshold and bypassing various problems attendant with assaying more concentrated samples, i.e., less diluted samples. Moreover, the buffer system and methods of the invention significantly increase sensitivity of the immunodetection assays without a corresponding loss in selectivity. The low conductivity conditions also provide a fluidic environment of low conductivity in which binding to non-antigen coated wells is dramatically reduced.

The present invention provides methods for detecting and for capturing autoantibodies in a biological sample. These novel methods can detect polyreactive autoantibodies having a low-avidity for a target antigen. In some embodiments, the methods can detect autoantibodies that have specific binding affinity to a target antigen selected from an amyloid-β antigen, a DNA antigen, a tubulin antigen, and a thyroglobulin antigen. The amyloid-β antigen may be in a form selected from a monomer, a dimer, an oligomer, cross-linked oligomers, and a fibril. The DNA antigen may be in a form selected from single-stranded DNA and double-stranded DNA. In some methods of the invention, a biological sample can be assayed for the presence of a plurality of distinct autoantibodies simultaneously using any multiplexed assays known in the art as enhanced by the teachings of the present disclosure. For instance, methods of the invention can be used to simultaneously detect autoantibodies of varying specificities so the immobilization of a plurality of distinct antigens on a solid phase is contemplated in those embodiments.

In some embodiments, the method comprises the steps of: (a) contacting the biological sample under a low conductivity condition with the target antigen for which the autoantibody has specific binding affinity; and (b) detecting the binding of said target antigen to said autoantibody in the biological sample. The target antigen is, in some embodiments, immobilized on a solid phase and the presence of binding is indicative of the autoantibody in the biological sample. In some embodiments, the method comprises, prior to step (b): washing the solid phase with a low conductivity buffer.

In some embodiments, the biological sample is selected from the group consisting of blood, serum, plasma, a fraction thereof, and a processed derivative thereof. In some embodiments, the biological sample is an IgG composition isolated from plasma, such as an intravenous IgG preparation (IVIG), an IgG preparation for subcutaneous administration, an IgG preparation for intramuscular preparation, etc. In some embodiments, the biological sample is derived from a human (e.g., human IVIG).

In some embodiments, the detection step (b) comprises: (i) contacting the biological sample with a species-specific antibody which binds to the autoantibody against the target antigen, wherein the species-specific antibody is specific for the species from which the biological sample was obtained under conditions sufficient for specific binding of the species-specific antibody to the corresponding autoantibody present; and (ii) detecting any complex comprising the target antigen bound to the corresponding autoantibody, which is bound to the species-specific antibody. In some embodiments, detection step (ii) comprises contacting the detectable moiety with an indicator reagent (e.g., a detectable moiety attached to the species-specific antibody).

In some embodiments, the species-specific antibody is conjugated to a detectable moiety. The detectable moiety may, in some embodiments, comprise a direct label. The direct label could comprise peroxidase. In other embodiments, the detectable moiety comprises an indirect label. In some embodiments, the species-specific antibody is selected from the IgG isotype.

In some embodiments, the autoantibodies to be assayed are of an isotype selected from IgG, IgA, and IgM. In preferred embodiments, the polyreactive, low-avidity autoantibodies to be detected are of the IgG isotype. In more preferred embodiments, the polyreactive, low-avidity autoantibodies are of the human IgG isotype.

In some embodiments, the biological sample is diluted at least 1,000 fold or at least 5,000 fold with a low conductivity dilution buffer prior to step (a). In certain embodiments, the methods described above further comprise, prior to step (a), blocking the plate with a low conductivity buffer. Detection may involve confirming the presence of an autoantibody of interest in some cases or quantifying the concentration of autoantibody(ies) of interest in other cases. Those of skill in the art would appreciate that the methods described herein have the capacity to detect or capture not only polyreactive, low-avidity autoantibodies but also autoantibodies that are monovalent.

In some embodiments, the biological sample is a fluid selected from blood, serum, plasma, urine, saliva, cerebral spinal fluid, and synovial fluid. Preferably, the biological sample is selected from whole blood, serum, plasma, intravenous IgG preparation (IVIG), or some fraction or processed derivatives thereof. In some embodiments, the biological sample is an IVIG manufacturing process intermediate.

BRIEF DESCRIPTION OF THE DRAWINGS

More particular descriptions of the invention are made by reference to certain exemplary embodiments thereof which are illustrated in the appended Figures. These Figures form a part of the specification. It is to be noted, however, that the appended Figures illustrate exemplary embodiments of the invention and therefore are not to be considered limiting in their scope.

FIG. 1 shows the measurement of anti-Aβ(1-40)IgG in samples of human plasma and IVIG preparation, respectively, using the exemplary assay described in Example 1. The binding curves correspond to measurements obtained for the dilution series of each sample type using 16 mS/cm or low conductivity conditions throughout the entire assay. Levels of anti-Aβ(1-40) IgG are expressed as blank-corrected OD.

FIG. 2 shows the measurement of anti-Aβ(1-42) IgG in eight lots of an IVIG manufacturing process intermediate using the exemplary assay described in Example 2. Levels of anti-Aβ(1-42) IgG are expressed as blank-corrected OD per mg of IgG.

FIG. 3 shows the measurement of anti-Aβ fibril IgG in eight lots of an IVIG manufacturing process intermediate using the exemplary embodiment described in Example 4. Levels of anti-Aβ(1-42) IgG are expressed as blank-corrected OD per mg of IgG.

FIG. 4 shows the measurement of anti-DNA IgG in samples of human plasma using the exemplary assay described in Example 5. The binding curves correspond to measurements obtained for the dilution series using 16 mS/cm or low conductivity conditions throughout the entire assay. Levels of anti-DNA IgG are expressed as blank-corrected OD.

FIG. 5 shows the measurement of anti-tubulin IgG in samples of human plasma using the exemplary assay described in Example 6. The binding curves correspond to measurements obtained for the dilution series using 16 mS/cm or low conductivity conditions throughout the entire assay. Levels of anti-tubulin IgG are expressed as blank-corrected OD.

FIG. 6 shows the measurement of anti-thyroglobulin IgG in samples of human plasma using the exemplary assay described in Example 7. The binding curves correspond to measurements obtained for the dilution series using 16 mS/cm or low conductivity conditions throughout the entire assay. Levels of anti-thyroglobulin IgG are expressed as blank-corrected OD.

FIG. 7 shows the measurement of anti-DNA IgG in a human reference plasma using the exemplary assay described in Example 8. The binding curves correspond to measurements obtained for the dilution series at varying salt concentrations [NaCl]: 0 mM, 20 mM, 40 mM, 60 mM, 80 mM, 100 mM, 120 mM, and 150 mM, and demonstrate increasing assay sensitivity with decreasing salt concentrations. Levels of anti-DNA IgG are expressed as blank-corrected OD.

FIG. 8 is a plot of the relative signal intensities against the conductivity of the assay buffers described in Example 8. The linear regression curve between conductivity and the logarithm of the signal intensity, bearing a square correlation coefficient of $R^2=0.98$, supports the existence of an inverse proportional relationship between conductivity and signal intensity.

FIG. 9 shows competition curves for anti-DNA and anti-tubulin IgG binding at low conductivity conditions in a comparative study provided in Example 9. The data obtained confirms that low conductivity of the assay buffers did not impact the specificity of the binding assays.

DETAILED DESCRIPTION OF THE INVENTION

The discovery that low conductivity conditions enhance assay sensitivity and improve selectivity can be applied as an adjunct to current technologies used in the clinic or laboratory for detecting a variety of different non-affinity maturated, polyreactive, human autoantibody IgG. It is contemplated that the present invention could also be used to improve the detection of non-affinity maturated, polyreactive autoantibodies of other non-human mammalian species. Also contemplated is the use of the presently described methods to capture low-avidity, polyreactive autoantibodies of interest from a given sample or as an adjunct to autoantibody purification methodologies known in the art.

Non-specific binding of non-affinity maturated autoantibodies, e.g. polyreactive or otherwise, to glass, metal, plastic or other materials used in conventional solid substrates is a well-known source of error in immunodetection. For example, human plasma contains relatively large amounts of non-affinity maturated, polyreactive antibodies specific for amyloid aggregates, their target antigen. The presence of such polyreactive autoantibodies as well as antibodies that bind non-specifically to assay substrates artifactually inflates the concentration of detected polyreactive autoantibodies of interest. Advantageously, the methods provided herein increase assay sensitivity for non-affinity maturated autoantibodies and decrease such autoantibodies' binding to the substrate by use of the low conductivity assay conditions taught herein.

Typically, the binding of antigens and antibodies, and subsequent washing of complexes formed thereof, in ELISA assays is performed at moderate to high conductivity, to reduce non-specific antigen antibody interactions. For example, biological samples are commonly diluted in phosphate buffered saline (PBS) or Tris buffered saline (TBS) prior to performing the ELISA assay. Both PBS (137 mM NaCl, 2.7 mM KCl, 10 mM Na2HPO4, 2 mM KH2PO4) and TBS (50 mM Tris, 150 mM NaCl) buffers have moderate ionic strengths, thought to be useful for increasing the stringency of an ELISA assay. Many ELISA protocols also perform binding and washing of the antigen-antibody complex in PBS or TBS buffer.

Advantageously, it is shown herein that the use of low conductivity solution conditions in autoantibody detection assays substantially increases the sensitivity of the assay without compromising the specificity, e.g., without causing an increase in non-specific binding ("background noise"). For example, as shown in FIG. 7, anti-DNA autoantibody detection assays performed under solution conditions containing 60 mM sodium chloride are about 100-fold more sensitive than assays performed under solution conditions containing 150 mM sodium chloride (as is present in TBS buffer). Even more striking, assays performed in the absence of salt (e.g., 0 mM sodium chloride) are nearly 10,000-fold more sensitive than assays performed under solution conditions containing 150 mM sodium chloride. Thus, in some embodiments, an autoantibody detection assay is described in which the solution conditions are maintained at low ionic strength (e.g., where the binding and/or wash buffers contain low levels of ionic components such as salts).

I. DEFINITIONS

An autoantibody, used interchangeably herein with the term "endogenous antibody," refers to an antibody produced by an organism and which binds to an antigen endogenous to that same organism. The methods described herein detect an "autoantibody in a biological sample," which is to be construed as an autoantibody produced by an organism and which binds to an antigen endogenous to that same organism, said organism being a source of biological material from which the biological sample was derived. In terms of structure, an autoantibody of the IgM isotype has five Fc regions and ten Fab regions; an autoantibody of the IgG isotype has one Fc region and two Fab regions; and an autoantibody of the IgA isotype has two Fc region and four Fab regions. As those of skill in the art would appreciate, autoantibodies detectable by the methods will include affinity maturated autoantibodies or non-affinity maturated autoantibodies as well as polyreactive autoantibodies or mono-reactive autoantibodies.

The term "autoantigen," used interchangeably with the term "endogenous antigen" and "self-antigen," is a constituent of an individual's body which triggers the production of antibodies in the same individual.

A "mono-reactive" antibody refers to an antibody in which the $F_{ab}$ region reacts with or binds to a single antigen.

A "polyreactive" antibody refers to an antibody in which the $F_{ab}$ region reacts with or binds to multiple antigens.

A "polyreactive autoantibody," as used herein, refers to an autoantibody in which the $F_{ab}$ region reacts with or binds to multiple antigens. In some embodiments, the polyreactive autoantibody is reactive with one or more self-antigens. In other embodiments, the polyreactive autoantibody is reactive with a self-antigen and a foreign antigen.

As used herein, a "non-affinity maturated autoantibody" refers to an autoantibody expressed by a B-cell which has not undergone affinity maturation. Affinity maturation is a process by which B cells that express antibodies with higher affinity for antigen(s) presented at the germinal centers are selected for activation. The process involves iterations of somatic hypermutation followed by affinity-based selection, operating to generate a population of B cells which express antibodies with higher affinities for their target antigens.

As used herein, the term "affinity" refers to the strength of an interaction between a single antigenic determinant on an antigen and its corresponding binding site on an antibody. It is the sum of the attractive and repulsive forces operating between the antigenic determinant and the corresponding binding site of the antibody. Affinity is described as a dissociation constant (e.g. $K_D$ or Kd) characterizing the antigen-antibody interaction. The higher the affinity of an antibody for an antigen, the lower the Kd.

As used herein, the term "avidity" is a characteristic that describes the overall strength of binding between an antibody and its target antigen, taking into account their interactions with one another at multiple sites. In some instances, the overall strength of binding between an antibody and its target antigen is greater than the sum of the individual bond affinities. To illustrate, for an antibody having multiple antigen binding sites that simultaneously interact with a single antigen, each individual binding interaction on its own can be readily broken. However, when an antibody and its target antigen are bound at multiple sites, the overall effect is synergistic because binding of such an antibody to its target antigen would be reinforced by the presence of other binding interactions when there is transient separation of a single binding site on the antibody from its corresponding antigenic determinant on the target antigen.

As used herein, an "amyloid-β antigen" is in a form selected from monomer, dimer, oligomer, an aggregate of cross-linked oligomers, and a fibril. The amyloid-β antigen may comprise a full length amyloid-β protein or a portion thereof, said portion comprising an antigenic determinant chosen to capture or detect the autoantibodies of interest. The Aβ oligomer may range in composition and correspond to an N-terminal sequence, C-terminal sequence, or any portion of the Aβ protein. In some embodiments, the amyloid-β antigen comprises an epitope within the exposed N-terminal six residues of the native and fibrillar forms of Aβ. See, Solomon et al. (1996) Proc Natl Acad Sci USA 93: 452-455. In other embodiments, the amyloid-β antigen is a form of amyloid-β-40 peptide (amino acids 1-40) selected from a monomer, dimer, oligomer, aggregate of cross-linked oligomers and a fibril. In other embodiments, the amyloid-β antigen is a form of amyloid-β-42 peptide (amino acids 1-42) selected from a monomer, dimer, oligomer, aggregate of cross-linked oligomers and a fibril.

The transformation of soluble proteins and peptides into insoluble amyloid fibrils reflects a series of conformational alterations that involve formation of amyloidogenic intermediates; self-association and stabilization of these components through interactions between β-sheets that lead to protofilaments/protofibrils; and, finally, interaction of the components to form the mature fibril. See, Serpell (2000) Biochim Biophys Acta 1502:15-30; Dobson (2004) Methods 34:4-14;

Makin et al. (2005) Proc Natl Acad Sci USA 102:315-320. It is therefore contemplated that the amyloid-β antigen selected can adopt any of the afore-mentioned transition states, e.g. amyloidogenic intermediates, protofilaments, or profibrils. In some embodiments, the amyloid-β antigen comprises sequence-specific linear epitope(s) exposed on the fibril as well as the partially unfolded amyloidogenic intermediate and native precursor protein. In other embodiments, the amyloid-β antigen comprises neoepitopes present on the fibril and assembly intermediates (e.g., antigenic regions buried in the native molecule which become exposed as a result of protein unfolding). In still other embodiments, the amyloid-β antigen comprises a generic conformational epitope(s) common to all fibrils, irrespective of primary structure. See, Hrncic et al. (2000) Am J. Pathol 157:1239-1246; O'Nuallain et al. (2002) Proc natl Acad Sci USA 99:1485-1490. Another exemplary amyloid-β antigen comprises a conformational epitope(s) common to amyloid β-40 peptide, light chains (LC), serum amyloid A (SAA), transthyretin (TTR), and islet amyloid polypeptide (IAPP) that is not present in the native non-fibrillar states of these amyloidogenic peptides.

As used herein, a "tubulin antigen" is in a form selected from monomer, dimer, oligomer, and aggregate. The tubulin antigen may comprise a full length tubulin protein or a portion thereof, said portion comprising an antigenic determinant chosen to capture or detect the autoantibodies of interest. The tubulin antigen may comprise one or more tubulin polypeptide of the subtype α, subtype β, subtype γ, subtype δ, or subtype ε. The tubulin antigen may range in composition and correspond to an N-terminal sequence, C-terminal sequence, or any portion of the tubulin protein. Any of these or other tubulin proteins can be used in the methods provided herein. In preferred embodiments, the tubulin antigen is derived from the same species as the autoantibodies being assayed.

As used herein, a "thyroglobulin antigen" may comprise a full length thyroglobulin protein or a portion thereof, said portion comprising an antigenic determinant chosen to capture or detect the autoantibodies of interest. The thyroglobulin antigen may range in composition and correspond to an N-terminal sequence, C-terminal sequence, or any portion of the thyroglobulin protein. Any of these or other thyroglobulin proteins can be used in the methods provided herein. In preferred embodiments, the thyroglobulin antigen is derived from the same species as the autoantibodies being assayed.

As used herein, a "DNA antigen" is in a form selected from single-stranded DNA and double-stranded DNA. The DNA antigen may range in composition and be of any length. In some embodiments, the DNA antigen is derived from the same species as the autoantibodies being assayed.

In the context of the present invention, a "target antigen" is an antigen selected to detect the autoantibodies of interest. The target antigen can be in a form selected from monomer, dimer, oligomer, polymer, and an aggregate. In preferred embodiments, the target antigen is derived from the same species as the autoantibodies being assayed. In select embodiments, the target antigen and the autoantibodies being assayed are both human.

The term "low conductivity" as used herein refers to a conductivity ranging from 0 mS/cm to less than 13 mS/cm, about 1 mS/cm to about 13 mS/cm, about 2 mS/cm to about 13 mS/cm, about 3 mS/cm to about 13 mS/cm, about 4 mS/cm to about 13 mS/cm, about 5 mS/cm to about 13 mS/cm, about 6 mS/cm to about 13 mS/cm, about 7 mS/cm to about 13 mS/cm, about 8 mS/cm to about 13 mS/cm, about 9 mS/cm to about 13 mS/cm, about 10 mS/cm to about 13 mS/cm, about 11 mS/cm to about 13 mS/cm, and about 12 mS/cm to about 13 mS/cm. Low conductivity buffers or conditions useful for the methods described herein can be selected from hypotonic, isotonic, or hypertonic formulations.

The term "hypotonic" describes a formulation with a tonicity substantially below that of blood. Tonicity can be measured using a vapor pressure or ice-freezing type osmometer, for example.

Low conductivity buffers or condition of the invention selected from hypotonic formulations will generally have an osmolality ranging from about 1 mOsm to less than about 250 mOsm. In some embodiments, low conductivity buffers or condition of the invention are characterized by osmolalities respectively and independently selected from about 10 mOsm to less than about 250 mOsm, about 20 mOsm to less than about 250 mOsm, about 30 mOsm to less than about 250 mOsm, about 40 mOsm to less than about 250 mOsm, about 50 mOsm to less than about 250 mOsm, about 60 mOsm to less than about 250 mOsm, about 70 mOsm to less than about 250 mOsm, about 80 mOsm to less than about 250 mOsm, about 90 mOsm to less than about 250 mOsm, about 100 mOsm to less than about 250 mOsm, about 110 mOsm to less than about 250 mOsm, about 120 mOsm to less than about 250 mOsm, about 130 mOsm to less than about 250 mOsm, about 140 mOsm to less than about 250 mOsm, about 150 mOsm to less than about 250 mOsm, about 160 mOsm to less than about 250 mOsm, about 170 mOsm to less than about 250 mOsm, about 180 mOsm to less than about 250 mOsm, about 190 mOsm to less than about 250 mOsm, about 200 mOsm to less than about 250 mOsm, about 210 mOsm to less than about 250 mOsm, about 220 mOsm to less than about 250 mOsm, about 230 mOsm to less than about 250 mOsm, about 240 mOsm to less than about 250 mOsm.

In some embodiments, the low conductivity buffers or condition selected from hypotonic formulations have osmolalities respectively and independently selected from a range of about 1-100 mOsm, about 1-75 mOsm, about 1-50 mOsm, and about 1-25 mOsm. In other embodiments, the low conductivity buffers or condition have osmolalities respectively and independently selected from a range of about 25-250 mOsm, about 50-225 mOsm, about 75-200 mOsm, about 100-175 mOsm, about 125-150 mOsm.

The term "isotonic" describes a formulation with a tonicity approximating that of blood. In some embodiments, the low conductivity buffers or condition selected from isotonic formulations have osmolalities respectively and independently selected from a range of about 250 mOsm to 350 mOsm. In some embodiments, the low conductivity buffers or condition selected from isotonic formulations have osmolalities respectively and independently selected from a range of about 250 mOsm to about 325 mOsm, about 250 mOsm to about 300 mOsm, about 250 mOsm to about 275 mOsm. In other embodiments, the low conductivity buffers or condition selected from isotonic formulations have osmolalities respectively and independently selected from a range of about 275 mOsm to about 350 mOsm, about 300 mOsm to about 350 mOsm, about 325 mOsm to about 350 mOsm. In still other embodiments, the low conductivity buffers or condition selected from isotonic formulations have osmolalities respectively and independently selected from a range of about 275 mOsm to about 325 mOsm.

The term "hypertonic" describes a formulation with a tonicity substantially above that of blood. In some embodiments, low conductivity buffers or condition of the invention are characterized by an osmolalities respectively and independently selected from a range of greater than 350 mOsm to about 2000 mOsm, greater than 350 mOsm to about 1950 mOsm, greater than 350 mOsm to about 1900 mOsm, greater than 350 mOsm to about 1850 mOsm, greater than 350 mOsm to about 1800 mOsm, greater than 350 mOsm to about 1750 mOsm, greater than 350 mOsm to about 1700 mOsm, greater than 350 mOsm to about 1650 mOsm, greater than 350 mOsm to about 1600 mOsm, greater than 350 mOsm to about 1550 mOsm, greater than 350 mOsm to about 1500 mOsm, greater than 350 mOsm to about 1450 mOsm, greater than 350 mOsm to about 1400 mOsm, greater than 350 mOsm to about 1350 mOsm, greater than 350 mOsm to about 1300 mOsm, greater than 350 mOsm to about 1250 mOsm, greater than 350 mOsm to about 1200 mOsm, greater than 350 mOsm to about 1150 mOsm, greater than 350 mOsm to about 1100 mOsm, greater than 350 mOsm to about 1050 mOsm, greater than 350 mOsm to about 1000 mOsm, greater than 350 mOsm to about 950 mOsm, greater than 350 mOsm to about 900 mOsm, greater than 350 mOsm to about 850 mOsm, greater than 350 mOsm to about 800 mOsm, greater than 350 mOsm to about 750 mOsm, greater than 350 mOsm to about 700 mOsm, greater than 350 mOsm to about 650 mOsm, greater than 350 mOsm to about 625 mOsm, greater than 350 mOsm to about 600 mOsm, greater than 350 mOsm to about 550 mOsm, greater than 350 mOsm to about 500 mOsm, greater than 350 mOsm to about 450 mOsm, greater than 350 mOsm to about 400 mOsm.

The terms "individual," "subject," and "patient," used interchangeably herein, refer to a mammal, including, but not limited to, murines, simians, humans, mammalian farm animals, mammalian sport animals, and mammalian pets. In preferred embodiments, the individual is a human.

The term "sample" as used herein refers to a biological sample obtained for the purpose of evaluation in vitro. In the methods of the present invention, the sample is derived from a biological fluid taken from one or more individuals of the same species. In preferred embodiments, the biological fluid is of human origin. Exemplary biological fluids include blood, serum, plasma, cerebrospinal fluid, synovial fluid, urine, or saliva. In preferred embodiments, the biological fluid is selected from whole blood, serum, plasma, and a fraction or processed derivative thereof (e.g., an IgG solution isolated from blood, plasma, pooled blood, or pooled plasma, such as IVIG).

The terms "dose" and "dosage" are used interchangeably herein. A dose refers to the amount of active ingredient given to an individual at each administration. The dose will vary depending on a number of factors, including frequency of administration; size and tolerance of the individual; severity of the condition; risk of side effects; and the route of administration. One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a saline solution for injection.

A "therapeutically effective" amount or dose or "sufficient/effective" amount or dose, is a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

The terms "therapy," "treatment," and "amelioration" refer to any reduction in the severity of symptoms or amount of amyloid aggregation, or improvement in cognitive function. As used herein, the terms "treat" and "prevent" are not intended to be absolute terms. Treatment can refer to any delay in onset, amelioration of symptoms, improvement in patient survival, increase in survival time or rate, etc. The effect of treatment can be compared to an individual or pool of individuals not receiving the treatment.

A "control" sample or value refers to a sample that serves as a reference, usually a known reference, for comparison to a test sample. For example, a test sample can be a reference sample of known IgG concentration. A control can also represent an average value gathered from a population of similar individuals, e.g., Alzheimer's disease patients, Parkinson's disease patients, Creutzfeldt-Jakob disease patients, etc. with a similar medical background, or of the same age, weight, etc. A control value can also be obtained from the same individual, e.g., from an earlier-obtained sample, prior to symptoms, or before or at different therapeutic time points. In some cases, controls can include comparisons within an individual or between individuals, e.g., comparison of anti-amyloid antibody titres with the titre of one or more known antibodies.

One of skill in the art will understand which controls are valuable in a given situation and be able to analyze data based on comparisons to control values. Controls are also valuable for determining the significance of data. For example, if values for a given parameter vary widely in controls, variation in test samples will not be considered as significant.

It is contemplated that the systems and methods of the present invention can be applied to single measurement detection assays as well as multiplexed assays. The term "multiplexed assay," as used herein, refers to an assay, such as those described in U.S. Pat. No. 5,763,158 or U.S. Pat. No. 5,981,180, capable of making different measurements simultaneously. "Different measurements" is understood to mean detection of a plurality of distinct analytes, or detection of a single analyte by a plurality of distinct bead subsets, or a combination of both. In this context, "simultaneously," is understood to mean that the multiple analytes are detected, or the single analyte is detected by different bead sets, or the combination of measurements, is performed in the same assay. Typically, a multiplexed assay will be performed in a single vessel containing several sets of particles (e.g., a pooled subset of particles), such that a single multiplexed assay will provide multiple read-outs of information.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

II. DETAILED DESCRIPTION

The present invention is suitable for use in assaying non-affinity maturated autoantibodies, e.g., polyreactive or otherwise, in a range of biological samples. Biological samples contemplated by the present invention include any fluid selected from blood, serum, plasma, urine, saliva, synovial fluid and cerebral spinal fluid. Preferably, the biological sample is selected from whole blood, serum, plasma, an IgG composition isolated from blood or plasma (e.g. intravenous IgG), or a fraction or processed derivative thereof.

The biological sample may be obtained by a variety of means. In some embodiments, the biological sample is collected or a biopsy is performed and the collected biological sample is tested in vitro. In certain embodiments, immunoglobulins present in the sample are enriched prior to detection. In other embodiments, immunoglobulins are not further enriched prior to detection. The sample can be further separated, e.g., into plasma and cellular matter, to isolate the antibody-containing fraction, although this step is not necessary. The sample can also be exposed to size filtration and/or chromatography methods. In some embodiments, the sample is exposed to thiophilic chromatography to remove non-immunoglobulin proteins from the sample.

In some embodiments of the invention, the biological sample is diluted to at least a 1/20 dilution, to at least a 1/1000 dilution, or to at least a 1/500,000 dilution.

As mentioned above, the method of the invention includes (a) contacting the biological sample under a low conductivity condition with the target antigen for which the non-affinity maturated autoantibody has specific binding affinity; and (b) detecting the binding of said target antigen to said autoantibody in the biological sample. The target antigen has been immobilized on a solid phase prior to contacting step (a). In some embodiments, the non-affinity maturated autoantibody detected is polyreactive. Detection of binding is therefore indicative of the non-affinity maturated autoantibody in the biological sample.

In some embodiments, detection step (b) comprises: (i) contacting the biological sample with a species-specific antibody which binds to the target antigen-specific non-affinity maturated autoantibody against the target antigen, wherein the species-specific antibody is specific for the species from which the biological sample was obtained under conditions sufficient for specific binding of the species-specific antibody to the corresponding target-antigen-specific autoantibody present; and (ii) detecting any complex comprising the target antigen bound to the corresponding target antigen-specific autoantibody, which is bound to the species-specific antibody. In some embodiments, the target antigen-specific non-affinity maturated autoantibody detected is polyreactive. The species is selected from any mammalian species, e.g. primate species, such as humans and chimpanzees; murines, such as rats and mice; canines; felines; bovines; ovines; equines; etc. In preferred embodiments, the species is human.

In some embodiments, detection step (b) comprises: (i) contacting the biological sample with a species-specific antibody which binds to the amyloid-β-specific non-affinity maturated autoantibody against the amyloid-β antigen, wherein the species-specific antibody is specific for the species from which the biological sample was obtained under conditions sufficient for specific binding of the species-specific antibody to the corresponding amyloid-β-specific autoantibody present; and (ii) detecting any complex comprising the amyloid-β antigen bound to the corresponding amyloid-β-specific autoantibody, which is bound to the species-specific antibody. In some embodiments, the amyloid-β-specific non-affinity maturated autoantibody detected is polyreactive. The species is selected from any mammalian species, e.g. primate species, such as humans and chimpanzees; murines, such as rats and mice; canines; felines; bovines; ovines; equines; etc. In preferred embodiments, the species is human.

In other embodiments, detection step (b) comprises: (i) contacting the biological sample with a species-specific antibody which binds to the DNA-specific non-affinity maturated autoantibody against the DNA antigen, wherein the species-specific antibody is specific for the species from which the biological sample was obtained under conditions sufficient for specific binding of the species-specific antibody to the corresponding DNA-specific autoantibody present; and (ii) detecting any complex comprising the DNA antigen bound to the corresponding DNA-specific autoantibody, which is bound to the species-specific antibody. In some embodiments, the DNA-specific non-affinity maturated autoantibody detected is polyreactive. The species is selected from any mammalian species, e.g. primate species, such as humans and chimpanzees; murines, such as rats and mice; canines; felines; bovines; ovines; equines; etc. In preferred embodiments, the species is human.

In still some embodiments, detection step (b) comprises: (i) contacting the biological sample with a species-specific antibody which binds to the tubulin-specific non-affinity maturated autoantibody against the tubulin antigen, wherein the species-specific antibody is specific for the species from which the biological sample was obtained under conditions sufficient for specific binding of the species-specific antibody to the corresponding tubulin-specific autoantibody present; and (ii) detecting any complex comprising the tubulin antigen bound to the corresponding tubulin-specific autoantibody, which is bound to the species-specific antibody. In some embodiments, the autoantibody detected is polyreactive. The species is selected from any mammalian species, e.g. primate species, such as humans and chimpanzees; murines, such as rats and mice; canines; felines; bovines; ovines; equines; etc. In preferred embodiments, the species is human.

In still further embodiments, detection step (b) comprises: (i) contacting the biological sample with a species-specific antibody which binds to the thyroglobulin-specific non-affinity maturated autoantibody against the thyroglobulin antigen, wherein the species-specific antibody is specific for the species from which the biological sample was obtained under conditions sufficient for specific binding of the species-specific antibody to the corresponding thyroglobulin-specific autoantibody present; and (ii) detecting any complex comprising the thyroglobulin antigen bound to the corresponding thyroglobulin-specific autoantibody, which is bound to the species-specific antibody. In some embodiments, the autoantibody detected is polyreactive. The species is selected from any mammalian species, e.g. primate species, such as humans and chimpanzees; murines, such as rats and mice; canines; felines; bovines; ovines; equines; etc. In preferred embodiments, the species is human.

In some embodiments, a method is provided for detecting a non-affinity maturated autoantibody present in a blood sample or fraction thereof having affinity for a target antigen, the method comprising the steps of (a) diluting the sample to a final immunoglobulin concentration of no more than 100 μg/mL, (b) contacting the diluted blood or serum sample with the target antigen under a first low conductivity solution condition to form a complex comprising the autoantibody and the target antigen, and (c) detecting the complex, wherein the first low conductivity solution condition has a conductivity of less than 11 mS/cm. In certain embodiments, the first low conductivity solution condition has a conductivity of less than 10 mS/cm, less than 9 mS/cm, less than 8 mS/cm, less than 7 mS/cm, less than 6 mS/cm, less than 5 mS/cm, less than 4 mS/cm, less than 3 mS/cm, less than 2 mS/cm, or less than 1 mS/cm.

In some embodiments, the method further comprises a step of (d) washing the complex formed in step (b) with a first wash buffer having a conductivity of less than 11 mS/cm. In some embodiments, the first wash buffer has a conductivity of less than 11 mS/cm. In certain embodiments, the first low conductivity solution condition has a conductivity of less than 10 mS/cm, less than 9 mS/cm, less than 8 mS/cm, less than 7 mS/cm, less than 6 mS/cm, less than 5 mS/cm, less than 4 mS/cm, less than 3 mS/cm, less than 2 mS/cm, or less than 1 mS/cm.

In some embodiments, the step of detecting the complex comprises the sub-steps of (i) contacting the complex comprising the autoantibody and the target antigen with an anti-human immunoglobulin antibody under a second low conductivity solution condition having a conductivity of less than 11 mS/cm to form a ternary complex, (ii) washing the ternary complex formed in sub-step (i) with a second wash buffer having a conductivity of less than 11 mS/cm, and (iii) detecting the presence of the anti-human immunoglobulin antibody. In some embodiments, the second low conductivity solution condition has a conductivity of less than 10 mS/cm, less than 9 mS/cm, less than 8 mS/cm, less than 7 mS/cm, less than 6 mS/cm, less than 5 mS/cm, less than 4 mS/cm, less than 3 mS/cm, less than 2 mS/cm, or less than 1 mS/cm. In some embodiments, the second wash buffer has a conductivity of less than 10 mS/cm, less than 9 mS/cm, less than 8 mS/cm, less than 7 mS/cm, less than 6 mS/cm, less than 5 mS/cm, less than 4 mS/cm, less than 3 mS/cm, less than 2 mS/cm, or less than 1 mS/cm. In some embodiments, detecting the presence of the anti-human immunoglobulin antibody comprises determining the relative concentration of the anti-human immunoglobulin antibody.

In the embodiments described above, where the species-specific antibody is conjugated to a detectable moiety, the detection step (ii) comprises contacting the detectable moiety with an indicator reagent.

In other embodiments, the method further comprises, prior to step (b): washing the solid phase with a low conductivity buffer.

Those of skill in the art will appreciate that a low conductivity buffer of the same or different composition may be used for one or more of the following purposes in any combination: washing the plate after immobilizing the target antigens; diluting the biological sample; blocking the plate; washing the complex(es) formed; contacting the complex with a secondary immunoglobulin; washing the ternary complex(es) formed.

The low conductivity blocking buffer may be characterized by a conductivity selected from a range of greater than 0 mS/cm to less than 13 mS/cm, about 1 mS/cm to about 13 mS/cm, about 2 mS/cm to about 13 mS/cm, about 3 mS/cm to about 13 mS/cm, about 4 mS/cm to about 13 mS/cm, about 5 mS/cm to about 13 mS/cm, about 6 mS/cm to about 13 mS/cm, about 7 mS/cm to about 13 mS/cm, about 8 mS/cm to about 13 mS/cm, about 9 mS/cm to about 13 mS/cm, about 10 mS/cm to about 13 mS/cm, about 11 mS/cm to about 13 mS/cm, and about 12 mS/cm to about 13 mS/cm.

In other embodiments, the low conductivity blocking buffer has a conductivity selected from a range of greater than 0 mS/cm to less than 12 mS/cm, greater than 0 mS/cm to less than about 11 mS/cm, greater than 0 mS/cm to less than about 10 mS/cm, greater than 0 mS/cm to less than about 9 mS/cm, greater than 0 mS/cm to less than about 8 mS/cm, greater than 0 mS/cm to less than about 7 mS/cm, greater than 0 mS/cm to less than about 6 mS/cm, greater than 0 mS/cm to less than about 5 mS/cm, greater than 0 mS/cm to less than about 4 mS/cm, greater than 0 mS/cm to less than about 3 mS/cm, greater than 0 mS/cm to less than about 2 mS/cm, greater than 0 mS/cm to less than about 1 mS/cm. In still other embodiments, the low conductivity blocking buffer has a conductivity selected from a range of about 1 mS/cm to about 12 mS/cm, about 2 mS/cm to about 11 mS/cm, about 3 mS/cm to about 10 mS/cm, about 4 mS/cm to about 9 mS/cm, about 5 mS/cm to about 8 mS/cm, and about 6 mS/cm to about 7 mS/cm. In yet other embodiments, the low conductivity blocking buffer has a conductivity of less than about 13 mS/cm, less than about 11 mS/cm, less than about 9 mS/cm, less than about 7 mS/cm, less than about 5 mS/cm, less than about 3 mS/cm, or less than about 1 mS/cm.

In some embodiments, the low conductivity condition has a conductivity selected from a range of greater than 0 mS/cm to less than 13 mS/cm, about 1 mS/cm to about 13 mS/cm, about 2 mS/cm to about 13 mS/cm, about 3 mS/cm to about 13 mS/cm, about 4 mS/cm to about 13 mS/cm, about 5 mS/cm to about 13 mS/cm, about 6 mS/cm to about 13 mS/cm, about 7 mS/cm to about 13 mS/cm, about 8 mS/cm to about 13 mS/cm, about 9 mS/cm to about 13 mS/cm, about 10 mS/cm to about 13 mS/cm, about 11 mS/cm to about 13 mS/cm, and about 12 mS/cm to about 13 mS/cm.

In other embodiments, the low conductivity condition has a conductivity selected from a range of greater than 0 mS/cm to less than 12 mS/cm, greater than 0 mS/cm to less than about 11 mS/cm, greater than 0 mS/cm to less than about 10 mS/cm, greater than 0 mS/cm to less than about 9 mS/cm, greater than 0 mS/cm to less than about 8 mS/cm, greater than 0 mS/cm to less than about 7 mS/cm, greater than 0 mS/cm to less than about 6 mS/cm, greater than 0 mS/cm to less than about 5 mS/cm, greater than 0 mS/cm to less than about 4 mS/cm, greater than 0 mS/cm to less than about 3 mS/cm, greater than 0 mS/cm to less than about 2 mS/cm, greater than 0 mS/cm to less than about 1 mS/cm. In still other embodiments, the low conductivity condition has a conductivity selected from a range of about 1 mS/cm to about 12 mS/cm, about 2 mS/cm to about 11 mS/cm, about 3 mS/cm to about 10 mS/cm, about 4 mS/cm to about 9 mS/cm, about 5 mS/cm to about 8 mS/cm, and about 6 mS/cm to about 7 mS/cm. In yet other embodiments, the low conductivity condition has a conductivity of less than about 13 mS/cm, less than about 11 mS/cm, less than about 9 mS/cm, less than about 7 mS/cm, less than about 5 mS/cm, less than about 3 mS/cm, or less than about 1 mS/cm.

In some embodiments, the low conductivity condition has a conductivity less than the conductivity of a 150 mM sodium chloride solution, less than the conductivity of a 120 mM sodium chloride solution, less than the conductivity of a 90 mM sodium chloride solution, less than the conductivity of a 60 mM sodium chloride solution, less than the conductivity of a 40 mM sodium chloride solution, or less than the conductivity of a 20 mM sodium chloride solution.

In some embodiments, the low conductivity wash buffer has a conductivity selected from a range of greater than 0 mS/cm to less than 13 mS/cm, about 1 mS/cm to about 13 mS/cm, about 2 mS/cm to about 13 mS/cm, about 3 mS/cm to about 13 mS/cm, about 4 mS/cm to about 13 mS/cm, about 5 mS/cm to about 13 mS/cm, about 6 mS/cm to about 13 mS/cm, about 7 mS/cm to about 13 mS/cm, about 8 mS/cm to about 13 mS/cm, about 9 mS/cm to about 13 mS/cm, about 10 mS/cm to about 13 mS/cm, about 11 mS/cm to about 13 mS/cm, and about 12 mS/cm to about 13 mS/cm.

In other embodiments, the low conductivity wash buffer has a conductivity selected from a range of greater than 0 mS/cm to less than 12 mS/cm, greater than 0 mS/cm to less than about 11 mS/cm, greater than 0 mS/cm to less than about 10 mS/cm, greater than 0 mS/cm to less than about 9 mS/cm, greater than 0 mS/cm to less than about 8 mS/cm, greater than 0 mS/cm to less than about 7 mS/cm, greater than 0 mS/cm to less than about 6 mS/cm, greater than 0 mS/cm to less than about 5 mS/cm, greater than 0 mS/cm to less than about 4 mS/cm, greater than 0 mS/cm to less than about 3 mS/cm, greater than 0 mS/cm to less than about 2 mS/cm, greater than 0 mS/cm to less than about 1 mS/cm. In still other embodiments, the low conductivity wash buffer has a conductivity selected from a range of about 1 mS/cm to about 12 mS/cm, about 2 mS/cm to about 11 mS/cm, about 3 mS/cm to about 10 mS/cm, about 4 mS/cm to about 9 mS/cm, about 5 mS/cm to about 8 mS/cm, and about 6 mS/cm to about 7 mS/cm. In yet other embodiments, the low conductivity wash buffer has a conductivity of less than about 13 mS/cm, less than about 11 mS/cm, less than about 9 mS/cm, less than about 7 mS/cm, less than about 5 mS/cm, less than about 3 mS/cm, or less than about 1 mS/cm.

In some embodiments, the low conductivity wash buffer has a conductivity less than the conductivity of a 150 mM sodium chloride solution, less than the conductivity of a 120 mM sodium chloride solution, less than the conductivity of a 90 mM sodium chloride solution, less than the conductivity of a 60 mM sodium chloride solution, less than the conductivity of a 40 mM sodium chloride solution, or less than the conductivity of a 20 mM sodium chloride solution.

In some embodiments, the low conductivity dilution buffer has a conductivity selected from a range of greater than 0 mS/cm to less than 13 mS/cm, about 1 mS/cm to about 13 mS/cm, about 2 mS/cm to about 13 mS/cm, about 3 mS/cm to about 13 mS/cm, about 4 mS/cm to about 13 mS/cm, about 5 mS/cm to about 13 mS/cm, about 6 mS/cm to about 13 mS/cm, about 7 mS/cm to about 13 mS/cm, about 8 mS/cm to about 13 mS/cm, about 9 mS/cm to about 13 mS/cm, about 10 mS/cm to about 13 mS/cm, about 11 mS/cm to about 13 mS/cm, and about 12 mS/cm to about 13 mS/cm.

In other embodiments, the low conductivity dilution buffer has a conductivity selected from a range of greater than 0 mS/cm to less than 12 mS/cm, greater than 0 mS/cm to less than about 11 mS/cm, greater than 0 mS/cm to less than about 10 mS/cm, greater than 0 mS/cm to less than about 9 mS/cm, greater than 0 mS/cm to less than about 8 mS/cm, greater than 0 mS/cm to less than about 7 mS/cm, greater than 0 mS/cm to less than about 6 mS/cm, greater than 0 mS/cm to less than about 5 mS/cm, greater than 0 mS/cm to less than about 4 mS/cm, greater than 0 mS/cm to less than about 3 mS/cm, greater than 0 mS/cm to less than about 2 mS/cm, greater than 0 mS/cm to less than about 1 mS/cm. In still other embodiments, the low conductivity dilution buffer has a conductivity selected from a range of about 1 mS/cm to about 12 mS/cm, about 2 mS/cm to about 11 mS/cm, about 3 mS/cm to about 10 mS/cm, about 4 mS/cm to about 9 mS/cm, about 5 mS/cm to about 8 mS/cm, and about 6 mS/cm to about 7 mS/cm. In yet other embodiments, the low conductivity dilution buffer has a conductivity of less than about 13 mS/cm, less than about 11 mS/cm, less than about 9 mS/cm, less than about 7 mS/cm, less than about 5 mS/cm, less than about 3 mS/cm, or less than about 1 mS/cm.

In some embodiments, the low conductivity dilution buffer has a conductivity less than the conductivity of a 150 mM sodium chloride solution, less than the conductivity of a 120 mM sodium chloride solution, less than the conductivity of a 90 mM sodium chloride solution, less than the conductivity of a 60 mM sodium chloride solution, less than the conductivity of a 40 mM sodium chloride solution, or less than the conductivity of a 20 mM sodium chloride solution.

The low conductivity buffer(s) used in the methods and systems of the present invention may be purchased from any commercial vendors, such as VWR, Fisher Scientific or Sigma Aldrich, or generated by those of ordinary skill in the art. In some embodiments, the low conductivity solution is buffered to physiological pH. In other embodiments, suitable low conductivity buffers contain one or more physiological salts selected from KCl, NaCl, $CaCl_2$, $KH_2PO_4$, $K_2HPO4$, $NaH_2PO_4$, $NaHCO_3$—$Na_2CO_3$, $Na_2HPO4$, $NaHCO_3$, and mixtures thereof. In other embodiments, the low conductivity buffers contain one or more non-physiological salts known in the art. Those of skill in the art will appreciate that low conductivity buffers useful in the presently described methods and systems may be selected from TAPS, CAPS, TES, MOPS, CHES, MES, bicine, BIS-TRIS propane, TRIS base, BIS TRIS, HEPES, other organic amine buffers, or various combinations thereof.

Exemplary low conductivity buffers useful in the present invention comprise varying concentrations of HEPES in some embodiments, varying concentrations of HEPES and Tween 20 in other embodiments, varying concentrations of HEPES, Tween 20, and $CaCl_2$ in still other embodiments, or varying concentrations of HEPES and Tween 20, NaCl, and $CaCl_2$ in yet other embodiments. In some embodiments, low conductivity buffers have a formulation selected from any of the following: 20 mM HEPES; 20 mM HEPES with 20 mM NaCl; 20 mM HEPES with 40 mM NaCl; 20 mM HEPES with 60 mM NaCl; 20 mM HEPES with 80 mM NaCl; 20 mM HEPES with 100 mM NaCl; 20 mM HEPES with 120 mM NaCl; 20 mM HEPES with 150 mM NaCl; 20 mM HEPES and 2 mM $CaCl_2$, 0.1% Tween 20; 20 mM HEPES and 0.1% Tween 20.

Other exemplary low conductivity buffers include a buffer of 80 mM NaCl, 1.8 mM KCl, 1.33 mM $KH_2PO_4$ and 5.33 mM $K_2HPO_4$, pH 7.4.+−.0.1; a buffer of 60 mM NaCl, 1.35 mM KCl, 1 mM $KH_2PO_4$ and 3.99 mM $K_2HPO_4$, pH 7.4.+−.0.1; a buffer of 70 mM NaCl, 20 mM $NaHCO_3$, 4 mM $KH_2PO_4$ and 2.6 mM $K_2HPO_4$, pH 7.4.+−.0.1; and a buffer of 65 mM NaCl, 1 mM $KH_2PO_4$ and 4 mM $K_2HPO_4$, pH 7.4.+−.0.1. In still other embodiments, the low conductivity buffers are substantially free of non-physiological salts.

The low conductivity wash buffer solution may be selected from any of the buffers described above. Furthermore, those of skill in the art guided by the present disclosure would be equipped to choose or generate a low conductivity buffer useful for the purpose of removing unbound antibodies and washing away antibodies weakly bound to nonspecific sites. Exemplary wash buffers may include a small amount of detergent diluted into Tris buffered saline or distilled water. In other embodiments, the wash buffers do not include a detergent.

Those of skill in the art will appreciate the present invention may be adapted to many conventional solid-phase detection methods. These include, without limitation, enzyme linked immunoabsorbent assay (ELISA), fluorescent immunosorbent assay (FIA), chemical linked immunosorbent assay (CLIA), and immunoblotting. For a review of the different immunoassays which may be used. See, *The Immunoassay Handbook*, David Wild, ed., Stockton Press, New York, 1994, the content of which is hereby expressly incorporated by reference in its entirety for all purposes.

A variety of detection methods known in the art may be used in conjunction with the present invention, as those of skill would appreciate. In some embodiments, the target antigen is immobilized on a solid support or surface such as a bead, plate, slide or microtiter dish. An aliquot of sample is added to the solid support and allowed to incubate with the target antigen in a liquid phase. An immunoglobulin (otherwise referred to herein as a secondary antibody) selected to recognize a constant region of the autoantibodies being assayed for is then added. In preferred embodiments, the secondary antibody is characterized by an IgG isotype. Alternatively, the secondary antibody is characterized by high affinity to some constant region of the autoantibody being assayed. After separating the solid support from the liquid phase, the support phase is examined for a detectable signal. The presence of the signal on the solid support indicates that autoantibodies to the target antigen on the support have bound its target.

The signal producing system is made up of one or more components, at least one of which is a label, which generate a detectable signal that relates to the amount of bound label. The label is a molecule that produces or which may be induced to produce a signal. Detectable labels suitable for such use include any composition detectable by spectroscopic, photochemical, biochemical, immunochemical, electrical, optical or chemical means. Examples of suitable labels include fluorescers, enzymes, chemiluminescers, photosensitizers or suspendable particles. The signal is detected and may be measured by detecting enzyme activity, luminescence or light absorbance.

Useful labels in the present invention include magnetic beads (e.g., DYNABEADS), fluorescent dyes (e.g., fluorescein isothiocyanate, Texas red, rhodamine, green fluorescent protein, and the like), radiolabels (e.g., 3H, 125I, 35S, 14C, or 32P), enzymes (e.g., horseradish peroxidase, alkaline phosphatase and others commonly used in an ELISA), and colorimetric labels such as colloidal gold or colored glass or plastic (e.g. polystyrene, polypropylene, latex) beads. A general overview of the applicable technology can be found in Harlow & Lane, Antibodies: A Laboratory Manual (1988), the content of which is hereby expressly incorporated by reference in its entirety for all purposes.

Although radiolabels may also be used and levels of radioactivity detected and measured using a scintillation counter, it is not preferred due to safety and environmental concerns. The most commonly used producing systems employ enzyme-mediated chromogenic or fluorophore-mediated fluorescent mechanisms. With chromogenic reporters, any bound enzyme label is then reacted with a substrate to yield a colored product that can be analyzed with a light microscope. Examples of additional enzymes labels which may be used include, without limitation, β-D-galactosidase, glucose-6-phosphate dehydrogenase ("G6PDH"), and glucose oxidase.

With fluorescent reporting systems, the fluorophores are conjugated to a probe or the secondary antibody and do not require a substrate to activate the enzyme as in chromogenic detection systems. Furthermore, fluorescent reporting systems are particularly useful in multiplex assays. Examples of fluorescer labels that can be used include, without limitation, fluorescein, isothiocyanate, rhodamine compounds, phycoerythrin, phycocyanin, allophycocyanin, o-phthaldehyde and fluorescamine. Chemiluminescers include e.g., isoluminol.

The amount or intensity of color, fluorescence, luminescence, or radioactivity present in the reaction (depending on the signal producing system used) should correlate with the concentration of autoantibodies in a sample. Quantification of optical density may be performed using spectrophotometric methods. Quantification of radiolabel signal may be performed using scintillation counting. Where enzyme labels are used, the enzymatic activity is dependent on several variables, including enzyme and substrate concentration, buffer, pH, temperature, and possibly light. Enzyme-substrate systems that can be employed are described in the art and may include, without limitation, DAB-HRP; metal-enhanced DAB-HRP; BCIP-AP; NBT-AP and glucose oxidase; 1-step NBT-BCIP and AP, etc.

Enzymes may be covalently linked to target antigen reactive antibodies for use in the methods of the invention using methods known to those of ordinary skill in the art. For example, alkaline phosphatase and horseradish peroxidase may be conjugated to antibodies using glutaraldehyde. Horseradish peroxidase may also be conjugated using the periodate method. Commercial kits for enzyme conjugating antibodies are widely available. Enzyme conjugated anti-human and anti-mouse immunoglobulin specific antibodies are available from multiple commercial sources.

Alternatively, indirect detection of the autoantibodies may be effected using avidin-biotin complex method, labeled streptavidin biotin method, or phosphatase-anti-phosphatase method as familiar to those of ordinary skill in the art.

Enzyme labeled antibodies produce different signal sources, depending on the substrate. Signal generation involves the addition of substrate to the reaction mixture. Common peroxidase substrates include 3,3'-diaminobenzidine (DAB), ABTS™-2,2'-azinobis(ethylbenzothiazoline-6-sulfonate)), OPD (O-phenylenediamine) and TMB (3,3', 5,5'-tetramethylbenzidine). p-nitrophenyl phosphate is a commonly used alkaline phosphatase substrate. Where alkaline phosphotase enzyme label is employed, the substrate is selected as a combination of nitro blue tetrazolium chloride (NBT) and 5-bromo-4-chloro-3-indolyl phosphate (BCIP). Where glucose oxidase enzyme label is employed, the substrate is selected to be nitro blue tetrazolium chloride. Where a β-galactosidase enzyme label is employed, the substrate is selected to be 5-bromo-4-chloro-3-indoyl-β-D-galactopyranoside (BCIG or X-Gal). During an incubation period, the enzyme gradually converts a proportion of the substrate to its end product. At the end of the incubation period, a stopping reagent may be added which stops enzyme activity. Signal strength is determined by measuring optical density, usually via spectrophotometer.

Alkaline phosphatase labeled antibodies may also be measured by fluorometry. Thus in the immunodetection methods of the present invention, the substrate 4-methylumbelliferyl phosphate (4-UMP) may be used. Alkaline phosphatase dephosphorylated 4-UMP to form 4-methylumbelliferone (4-MU), the fluorophore. Incident light is at 365 nm and emitted light is at 448 nm.

Throughout the assays, incubation and/or washing steps may be required after each combination of reagents. Incubation steps can vary from about 5 seconds to several hours, e.g., from about 5 minutes to about 24 hours. However, the incubation time will depend upon the assay format, antibody, volume of solution, concentrations, and the like. Usually, the assays will be carried out at ambient temperature, although they can be conducted over a range of temperatures, such as 10° C. to 40° C.

In some embodiments, at least one control is run alongside the sample, and compared for amount of antibody and/or level of binding. In other embodiments, the result of the assay may be compared to a control level previously established for the system of interest. For example, a positive control can include the same biological sample obtained from an individual or group of individuals that is known to have an amyloid-related disease. Another example of a suitable positive control is a known anti-amyloid monoclonal antibody for comparison. An exemplary negative control can include the same biological sample obtained from an individual or group of individuals that have low risk of developing the amyloid related disease. Another example of a suitable negative control is a known antibody specific for a non-amyloid antigen.

Using such methods, and correlating a relatively high level of anti-amyloid antibodies with an increased likelihood that the subject has or is at high risk of developing an amyloid-related autoimmune disorder, one of skill can diagnose an amyloid-related autoimmune disease in the subject.

The above methods can be applied to selecting a patient group for an amyloid-related disease therapy. For example, the level of anti-amyloid antibodies can be determined in a plurality of individuals. As explained above, those individuals determined to have relatively high levels of anti-amyloid antibodies can be selected for treatment. In some embodiments, the level of anti-amyloid antibodies is detected periodically over a course of treatment. In some embodiments, the treatment comprises administration of IVIG.

Alzheimer's Disease and Other Amyloid-Related Disorders

Amyloid proteins and abnormal protein aggregates play a role in a number of different diseases and conditions. Methods of the invention enable the detection of certain non-affinity maturated, polyreactive autoantibodies against various forms of amyloid antigens or polypeptide aggregates. It is contemplated that detection of certain non-affinity maturated, anti-amyloid autoantibodies will facilitate one of skill in the art in making a diagnosis or determination of the course of therapy for any disease wherein an amyloid protein serves as a disease marker. As such, methods of the invention comprise the detection of anti-amyloid autoantibodies followed by the making of a diagnosis in some embodiments. Methods of the invention may comprise the detection of anti-amyloid autoantibodies followed by the making of a diagnosis and further comprising a step of determining the course of therapy to ameliorate the Alzheimer's disease or other amyloid-related autoimmune disorders. It is further contemplated that some embodiments of the invention described herein may comprise detection of autoantibodies of interest followed by administering a therapeutically effective amount of IVIG to a patient in need thereof Amyloid related disorders include not only Alzheimer's Disease (AD), but also Type 2 diabetes mellitus, Parkinson's disease, Transmissible spongiform encephalopathy, Huntington's Disease, Medullary carcinoma of the thyroid, Cardiac arrhythmias, Atherosclerosis, Rheumatoid arthritis, Aortic medial amyloid, Prolactinomas, Familial amyloid polyneuropathy, Hereditary non-neuropathic systemic amyloidosis, Dialysis related amyloidosis, Finnish amyloidosis, Lattice corneal dystrophy, Cerebral amyloid angiopathy, Cerebral amyloid angiopathy (Icelandic type), and systemic AL amyloidosis. In some embodiments, the disease or condition correlated with the target antigen is Alzheimer's disease.

Accordingly, the invention can be used to detect and/or capture autoantibodies against specific forms of amyloid antigens and amyloid aggregates found in amyloid-related disorders. In addition, the methods disclosed herein can be applied to detection of antibodies against abnormal protein aggregates formed from Beta amyloid (Aβ; Abeta), Islet amyloid polypeptide (IAPP; Amylin), Alpha-synuclein (SNCA), Major Prion Protein (PrP), Huntingtin (HD), Calcitonin (CCP), Atrial natriuretic factor (ANF), Apolipoprotein AI (Apo-A1), Serum amyloid A protein (SAA), Medin amyloid (fragment of Milk fat globule-EGF factor 8 protein; MFG-E8), Prolactin (PRL), Transthyretin (ATTR), Lysozyme C (1,4-beta-N-acetylmuramidase C), Beta 2 microglobulin 032M), Gelsolin (AGEL), Transforming growth factor-beta-induced protein ig-h3 (Beta ig-h3; Keratoepithelin), Cystatin C(CST3), Immunoglobulin light chain (AL), proteins having polyQ repeats, Tau protein (Tau), and other amyloid proteins.

In some embodiments, the methods described herein can be applied to detection of autoantibodies against any amyloidogenic proteins in the art, such as those listed in the following table:

| Amyloid Nomenclature: Amyloid fibril proteins and their precursors in humans* | |
| --- | --- |
| Amyloid Protein | Protein Precursor |
| AL | Immunoglobulin light chain |
| AH | Immunoglobulin heavy chain |
| ATTR | Transthyretin |
| $A\beta_2 M$ | $\beta_2$-microglobulin |
| AA | (Apo)serum AA |
| AapoAI | Apolipoprotein AI |
| AApo AII | Apolipoprotein AII |
| Agel | Gelsolin |
| Alys | Lysozyme |
| Afib | Fibrinogen α-chain |
| Acys | Cystatin C |
| Abri | ABriPP |
| Adan | ADanPP |
| AprP | Prion protein |
| ACal | (Pro)calcitonin |
| AIAPP | Islet amyloid polypeptide |
| AANF | Atrial natriuretic factor |
| APro | Prolactin |
| AIns | Insulin |
| Amed | Lactadherin |
| AKer | Kerato-epithelin |
| A(Pin) | Unknown |
| ALac | Lactoferrin |

*Modified from Westermark et al., 2002

Irrespective of their varied amino acid sequences, sources of origin, or biologic functions, all types of fibrils share virtually identical tinctorial and ultrastructural features, e.g., when stained by the diazobenzadine sulfonate dye Congo red and examined by polarizing microscopy, fibrils exhibit a characteristic green birefringence (see, Westermark et al. (2002) Amyloid J Protein Folding Disord 9:197-200) and their interaction with thioflavin T (ThT) results in a 120 nm red shift in the excitation spectrum of this benzothiazole compound (see, LeVine et al. (1995) Int J Exp Clin Invest 2:1-6). The demonstration that all fibrils, regardless of protein composition, share generic conformational epitopes has provided evidence for the presence of structural commonalities amongst these molecules. It is contemplated that the methods described herein can be used to detect autoantibodies which specifically recognize antigenic determinants expressed on amyloid fibrils or soluble oligomeric assembly intermediates via selection of the appropriate target antigen(s).

In certain embodiments of the methods provided herein, detection of the presence or level of a particular amyloid protein is useful to diagnose a particular disease or condition, or to select a candidate for the treatment of a particular disease or condition. Non-limiting examples of amyloid-disease correlations that are known in the art are found in Table 1. In certain embodiments, the detection of the presence or level of a non-affinity maturated antibody specific for the amyloid protein listed in Table 1 will be diagnostic of the corresponding disease listed.

late with family history. In many cases, an absolutely definitive diagnosis is considered unfeasible. Observable symptoms of AD include disruptive memory loss, differences in ability to solve problems, confusion as to time or place, trouble completing routine tasks, social withdrawal, and mood changes. These correlate with physical manifestations of the disease such as increased amyloid plaque formation and overall decrease in brain volume.

Therapies for Alzheimer's Disease and Other Amyloid-Related Diseases and Disorders In some embodiments of the invention, the methods described herein further comprise determining a prognosis for disease progression or a step of assigning a course of treatment or administering a treatment to the subject. Generally, the course of treatment will be prescribed when the level of anti-amyloid antibodies in the biological sample is above a control threshold (e.g., a threshold indicating a high likelihood or progression of the disease), or more closely resembles a positive control (e.g., a control level from a group or individual having experienced progression of the disease) than to a negative control (e.g., a control level from a group or individual not having experienced progression of the disease).

Treatments for amyloid-related diseases and conditions, such as AD, are typically focused on cognitive and mood

TABLE 1

Non-limiting examples of amyloid proteins associated with specific diseases.

| Disease | Amyloid Protein | GenBank Accession | UniProt Accession |
|---|---|---|---|
| Alzheimer's disease | Beta amyloid (Aβ; Abeta) | NP_000475 | P05067 |
| Type 2 diabetes mellitus | Islet amyloid polypeptide (IAPP; Amylin) | NP_000406 | P10997 |
| Parkinson's disease | Alpha-synuclein (SNCA) | NP_000336 | P37840 |
| Transmissible spongiform encephalopathy (e.g., Creutzfeldt-Jakob disease) | Major Prion Protein (PrP) | NP_000302 | P04156 |
| Huntington's Disease | Huntingtin (HD) | NP_002102 | P42858 |
| Medullary carcinoma of the thyroid | Calcitonin (CCP) | NP_001029124 | P01258 |
| Cardiac arrhythmias, Isolated atrial amyloidosis | Atrial natriuretic factor (ANF) | NP_006163 | P01160 |
| Atherosclerosis | Apolipoprotein AI (Apo-A1) | NP_000030 | P02647 |
| Rheumatoid arthritis | Serum amyloid A protein (SAA) | NP_954630 | P02735 |
| Aortic medial amyloid | Medin amyloid (fragment of Milk fat globule-EGF factor 8 protein; MFG-E8) | NP_005919 | Q08431 |
| Prolactinomas | Prolactin (PRL) | NP_000939 | P01236 |
| Familial amyloid polyneuropathy | Transthyretin (ATTR) | NP_000362 | P02766 |
| Hereditary non-neuropathic systemic amyloidosis | Lysozyme C (1,4-beta-N-acetylmuramidase C) | NP_000230 | P61626 |
| Dialysis related amyloidosis | Beta 2 microglobulin (β2M) | NP_004039 | P61769 |
| Finnish amyloidosis | Gelsolin (AGEL) | NP_000168 | P06396 |
| Lattice corneal dystrophy | Transforming growth factor-beta-induced protein ig-h3 (Beta ig-h3; Keratoepithelin) | NP_000349 | Q15582 |
| Cerebral amyloid angiopathy | Beta amyloid (Aβ; Abeta) | NP_000475 | P05067 |
| Cerebral amyloid angiopathy (Icelandic type) | Cystatin C (CST3) | NP_000090 | P01034 |
| systemic AL amyloidosis | Immunoglobulin light chain (AL) | | |

Detection of specific auto-antibodies, such as anti-Aβ oligomers in the case of AD and Parkinson's, can be used in diagnosis or risk factor assessment. The diagnostic methods of the invention can be applied to individuals considered at risk for developing an amyloid-related disorder, e.g., based on age, family history, cognitive symptoms, etc., as can be determined by one of skill in medicine.

Risk factors and symptoms of amyloid-related disorders will be best recognized by a skilled medical practitioner. Risk of developing these disorders increases with age, and corresymptoms of the disease. Early treatment and prevention regimes include physical and social activity, memory games, and puzzle and problem solving. Pharmaceutical therapies for symptomatic individuals include cholinesterase inhibitors (to address reduced acetylcholine), partial glutamate antagonists (e.g., Memantine), and psychiatric drugs (e.g., antipsychotics, sleep aides, anxiolytics, and beta-blockers). Cholinesterase inhibitors include Aricept® (donepezil hydrochloride), Exelon® (rivastigmine), Razadyne® (galantamine), and Cognex® (tacrine).

It has also been observed that pooled immunoglobulin preparations (e.g., IVIG) can be effective for improving AD symptoms. For example, the preparation of IVIG (intravenous immunoglobulin) is well known in the art. Methods for isolating IgG from pooled plasma are found, for example, in U.S. Patent Application Publication Nos. 2010/0330071 and 2011/0293638. Briefly, IVIG is formed by pooling blood or plasma donated from more than one individual (e.g., more than 1,000 individuals), separating the plasma fraction, and enriching for IgG immunoglobulin using a combination of chromatography, ultrafiltration, and diafiltration. IVIG is typically administered by intravenous infusion. Methods of treating AD, Parkinson's, and other protein aggregation disorders using IVIG are disclosed in US Pub. Nos. 2009/0148463 and 2009/0221017.

Detection of specific auto-antibodies, such as those against Aβ oligomers in the case of AD and Parkinson's, can be used in diagnosis or risk factor assessment. The diagnostic methods of the invention can be applied to individuals considered at risk for developing an amyloid-related disorder, e.g., based on age, family history, cognitive symptoms, etc., as can be determined by one of skill in medicine.

Risk factors and symptoms of amyloid-related disorders will be best recognized by a skilled medical practitioner. Risk of developing these disorders increases with age, and correlate with family history. In many cases, an absolutely definitive diagnosis is considered unfeasible. Observable symptoms of AD include disruptive memory loss, differences in ability to solve problems, confusion as to time or place, trouble completing routine tasks, social withdrawal, and mood changes. These correlate with physical manifestations of the disease such as increased amyloid plaque formation and overall decrease in brain volume.

In other embodiments of the invention, the methods of detection are used to monitor or generate a prognosis for disease progression associated, the control is from an individual or group of individuals that experienced progression of the disease, such that a similar or increased level of the remaining complex relative to control is indicative of a high likelihood or progression of the disease. In some embodiments, the control is from an individual or group of individuals that did not experience progression of the disease, such that a similar level of the remaining complex relative to control is indicative of a low likelihood of progression of the disease. In yet another embodiment, the control is from the same patient taken at an earlier time, such that an increased level of the remaining complex relative to control is indicative of a high likelihood or progression of the disease. In certain embodiments, the previous sample may have been taken about 1 month prior, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 month prior, or 4, 5, 6, 7, 8, 9, 10 or more years prior. One of skill will understand how to select at least one appropriate control and interpret the results accordingly.

Therapies for Systemic Lupus Erythematosus and Other DNA-Related Diseases and Disorders In some embodiments of the invention, the methods described herein further comprise determining a prognosis for disease progression or a step of assigning a course of treatment or administering a treatment to the subject. Generally, the course of treatment will be prescribed when the level of anti-DNA antibodies in the biological sample is above a control threshold (e.g., a threshold indicating a high likelihood or progression of the disease), or more closely resembles a positive control (e.g., a control level from a group or individual having experienced progression of the disease) than to a negative control (e.g., a control level from a group or individual not having experienced progression of the disease).

Therapies for DNA-related diseases and conditions, such as systemic lupus erythematosus, are known in the art. Pharmaceutical therapies for symptomatic individuals include nonsteroidal anti-inflammatory drugs (NSAIDs) such as ibuprofen and naproxen, antimalarials such as hydroxychloroquine (Plaquenil™), corticosteroids such as prednisone (Deltasone™), hydrocortisone, methylprednisolone (Medrol™), and dexamethasone (Decadron™, Hexadrol™), immunosuppressives such as cyclophosphamide (Cytoxan™) and mycophenolate mofetil (CellCept™), BLyS-specific inhibitors such as Belimumab (Benlysta®), methotrexate (Folex, Mexate, Rheumatrex), a disease-modifying antirheumatic drug, may be used to help control the disease. Other treatments may include hormonal therapies such as dehydroepiandrosterone (DHEA) and intravenous immunoglobulin, which is also useful for controlling lupus, particularly in cases when other treatments have failed to address the symptoms.

Detection of specific auto-antibodies, such as anti-dsDNA in the case of systemic lupus erythematosus, can be used in diagnosis or risk factor assessment. The diagnostic methods of the invention can be applied to individuals considered at risk for developing systemic lupus erythematosus, e.g., based on genetics, presence of an autoantibody such as anti-Sm, anti-RNP, anti-Ro (SSA), and anti-La (SSB) autoantibodies above a control threshold, exposure to infectious agents such as viruses such as the Epstein-Barr virus, and sunlight, stress, hormones, cigarette, smoke, or certain drugs, symptoms, etc., as can be determined by one of skill in medicine.

Risk factors and symptoms of DNA-related autoimmune disorders will be best recognized by a skilled medical practitioner. In many cases, an absolutely definitive diagnosis is considered unfeasible. Symptoms of systemic lupus erythematosus may be mild to severe and may include one or more of the following, without exclusion: painful or swollen joints (arthritis), unexplained fever, extreme fatigue, red skin rash across the nose and cheeks, face, ears, upper arms, shoulders, chest, hands, photosensitivity, chest pain, hair loss, anemia, mouth ulcers, pale or purple fingers from cold and stress, headaches, dizziness, depression, confusion, or seizures. In other embodiments of the invention, the methods of detection are used to monitor or generate a prognosis for disease progression associated, the control is from an individual or group of individuals that experienced progression of the disease, such that a similar or increased level of the remaining complex relative to control is indicative of a high likelihood or progression of the disease. In some embodiments, the control is from an individual or group of individuals that did not experience progression of the disease, such that a similar level of the remaining complex relative to control is indicative of a low likelihood of progression of the disease. In yet another embodiment, the control is from the same patient taken at an earlier time, such that an increased level of the remaining complex relative to control is indicative of a high likelihood or progression of the disease. In certain embodiments, the previous sample may have been taken about 1 month prior, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 month prior, or 3, 4, 5, 6, 7, 8, 9, 10 or more years prior. One of skill will understand how to select at least one appropriate control and interpret the results accordingly.

Therapies for Thyroiditis and Other Thyroglobulin-Related or Tubulin-Related Diseases and Disorders In some embodiments of the invention, the methods described herein further comprise determining a prognosis for disease progression or a step of assigning a course of treatment or administering a treatment to the subject. Generally, the course of treatment will be prescribed when the level of anti-thyroglobulin or anti-tubulin autoantibodies in the biological sample is above a control threshold (e.g., a threshold indicating a high likelihood or progression of the disease), or more closely resembles a positive control (e.g., a control level from a group or individual having experienced progression of the disease) than to a negative control (e.g., a control level from a group or individual not having experienced progression of the disease).

Therapies for thyroglobulin-related diseases and conditions, such as thyroiditis, e.g. Graves disease, Hashimoto's thyroiditis, hypothyroidism, thyroid cancer, thyrotoxicosis, are known in the art. Pharmaceutical therapies for symptomatic individuals include hormone replacement such as levothyroxine treatment (Levothroid™, Levoxyl™, Synthroid™), specialized diet, and supplementation, which may be used to help control the disease. Other treatments include intravenous immunoglobulin, which has demonstrated effect in the treatment of preclinical hypothyroidism in patients with Hashimoto's thyroiditis.

Detection of specific auto-antibodies, such as anti-thyroglobulin in the case of Hashimoto's thyroiditis, can be used in diagnosis or risk factor assessment. The diagnostic methods of the invention can be applied to individuals considered at risk for developing Hashimoto's thyroiditis, e.g., based on genetics, presence of an autoantibody such as anti-thyroid peroxidase autoantibodies above a control threshold, TSH levels, symptoms, etc., as can be determined by one of skill in medicine.

Risk factors and symptoms of thyroglobulin-related autoimmune disorders will be best recognized by a skilled medical practitioner. In many cases, an absolutely definitive diagnosis is considered unfeasible. Symptoms of Hashimoto's thyroiditis may be mild to severe and may include one or more of the following, without exclusion: Symptoms of Hashimoto's thyroiditis, the most common form of autoimmune hypothyroidism, may include swollen thyroid gland, chronic fatigue, increased sensitivity to cold, constipation depression, puffy face, hoarse voice, elevated blood cholesterol level, muscle aches, tenderness, and stiffness, muscle weakness, menorrhagia, dry hair and skin, lack of concentration, swelling of the feet or legs, and weight gain.

In other embodiments of the invention, the methods of detection are used to monitor or generate a prognosis for disease progression associated, the control is from an individual or group of individuals that experienced progression of the disease, such that a similar or increased level of the remaining complex relative to control is indicative of a high likelihood or progression of the disease. In some embodiments, the control is from an individual or group of individuals that did not experience progression of the disease, such that a similar level of the remaining complex relative to control is indicative of a low likelihood of progression of the disease. In yet another embodiment, the control is from the same patient taken at an earlier time, such that an increased level of the remaining complex relative to control is indicative of a high likelihood or progression of the disease. In certain embodiments, the previous sample may have been taken about 1 month prior, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 month prior, or 4, 5, 6, 7, 8, 9, 10 or more years prior. One of skill will understand how to select at least one appropriate control and interpret the results accordingly.

Pharmaceutical Compositions and Dosages

It is contemplated that the methods described herein can be used to standardize or quantify the amount of a non-affinity maturated autoantibody of interest in a biological sample, selected from the types described herein, which can then be administered to a subject in need thereof for therapeutic effect. In some embodiments, the autoantibody of interest is polyreactive. Alternatively, the methods described herein are used to capture non-affinity maturated autoantibodies of interest from a biological sample so as to be reconstituted in a formulation for administration to a subject in need thereof. A pharmaceutical composition comprising immunoglobulin, e.g. an enriched immunoglobulin preparation comprising heterogeneous human antibodies can be administered by a variety of methods known in the art. The route and/or mode of administration vary depending upon the desired results, but will typically be intravenous, intramuscular, intraperitoneal, or subcutaneous. The pharmaceutical composition can include an acceptable carrier suitable for intravenous, intramuscular, subcutaneous, parenteral, spinal or epidermal administration (e.g., by injection or infusion).

Proper fluidity of the composition can be maintained, for example, by use of coating such as lecithin, by maintenance of required particle size in the case of dispersion and by use of surfactants. In some cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., *Remington: The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Typically, a therapeutically effective dose or efficacious dose of the immunoglobulin preparation is employed in the pharmaceutical compositions of the invention. The pharmaceutical composition can be formulated into dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It can be advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels can be varied so as to obtain an amount of the active ingredient which is effective to achieve the desired therapeutic response for a particular patient without being toxic to the patient. A physician can start doses of the pharmaceutical composition at levels lower than that required to achieve the desired therapeutic effect and gradually increase the dosage until the desired effect is achieved. In general, effective doses vary depending upon many different factors, including the specific disease or condition to be treated, its severity, physiological state of the patient, other medications administered, and whether treatment is prophylactic or therapeutic. An exemplary treatment regime entails administration once per every two weeks or once a month or once every 3 to 6 months.

The composition can be administered on multiple occasions. Intervals between single dosages can be weekly, monthly or yearly. Intervals can also be irregular as indicated by measuring therapeutic progress in the patient. Dosage and frequency can vary depending on the half-life of the antibodies in the patient.

In the case of an immunoglobulin preparation, intravenous immunoglobulin (IVIG) is commonly used. The IVIG formulation is designed for administration by injection. Because the IgG preparation of this invention has achieved an exceptionally high immunoglobulin concentration (for example 10% w/v in some embodiments, 15% w/v in other embodiments, 20% w/v in still other embodiments, and up to 25% w/v in still further embodiments), which significantly reduces the volume for a therapeutically effective dose, the composition of the present invention are particularly advantageous for subcutaneous and/or intramuscular administration to a patient, as well as intravenous administration.

The term "effective amount" refers to an amount of an immunoglobulin, particularly IgG, preparation that results in an improvement or remediation of a medical condition being treated in the subject (e.g., Alzheimer's disease, Parkinson's disease, systemic lupus erythematosus, thyroiditis, autoimmune liver disorders, autoimmune hearing loss, and autoimmune thyroid diseases, etc.). An effective amount to be administered to the subject can be determined by a physician with consideration of individual differences in age, weight, disease severity, route of administration (e.g., intravenous v. subcutaneous) and response to the therapy. In certain embodiments, an immunoglobulin preparation of this invention can be administered to a subject at about 300 to about 600 mg/kilogram every 3 to 4 weeks based on clinical response. For intravenous administration, an exemplary initial infusion rate would be 0.5 mL/kg/hr (0.8 mg/kg/min) for 30 minutes whereas the exemplary maintenance infusion rate would be to increase the rate every 30 minutes if tolerated up to 5 mL/kg/hr (8 mg/kg/min).

For subcutaneous administration, an exemplary dose is 1.37 times previous intravenous dose divided by the number of weeks between intravenous doses whereas an exemplary maintenance dose is based on clinical response and target IgG trough level. For subcutaneous administration to individuals of 40 kg body weight and greater, an exemplary initial infusion rate is 30 mL/site at 20 mL/hr/site whereas an exemplary maintenance infusion rate is 30 mL/site at 20-30 mL/hr/site. For subcutaneous administration to individuals of less than 40 kg body weight, an exemplary initial infusion rate is 20 mL/site at 15 mL/hr/site whereas an exemplary maintenance infusion rate is 20 mL/site at 15-20 mL/hr/site. In other embodiments, the doses of the immunoglobulin preparation can be greater or less. Clinicians familiar with the diseases treated by IgG preparations can determine the appropriate dose for a patient according to criteria known in the art.

In accordance with the present invention, the time needed to complete a course of the treatment can be determined by a physician and may range from as short as one day to more than a month. In certain embodiments, a course of treatment can be from 1 to 6 months.

Kits

The invention further provides kits for the detection and/or isolation of non-affinity maturated autoantibodies, including polyreactive autoantibodies. The kits can be used for diagnosis of any autoimmune disorders, and identification of an individual susceptible to a particular method of therapy, such as with IVIG.

Kits will typically include instructions for use in written or electronic format, and standard reagents, solutions and buffers for the desired assay. The kit can optionally include standard controls or consumable labware, such as ELISA plates, chromatography tools, containers, and reaction vessels. The kit can also include devices for collection of a biological sample, e.g., syringes and blood fractionation devices.

The kits of the invention can include materials described herein for the detection of non-affinity maturated, polyreactive antibodies specific for any endogenous target antigen, including without exclusion, DNA, tubulin, thyroglobulin, and amyloid. The kit can include thiophilic chromatography reagents and appropriate wash and elution buffers to separate IgG from other proteins in the sample.

The kit can also include materials to separate non-affinity maturated autoantibodies of interest from non-specific antibodies. Such materials can include a solid support conjugated to the desired form of target antigen, e.g., monomeric, oligomeric (globular), polymeric, or aggregate. The solid support can be a bead, a chromatography stationary phase (e.g., agarose, silica, etc.), an ELISA plate, etc. The materials can also in some embodiments include at least one chaotropic wash buffer, to separate and remove low affinity antibodies from the amyloid-conjugated support after detection for reconstitution into a formulation for therapeutic use or further processing.

EXAMPLES

Examples are provided below to illustrate the present invention. These examples are not meant to constrain the present invention to any particular application or theory of operation.

Example 1

Measurement of Anti-Amyloid(1-40) (Aβ40) IgG in Plasma and in an Intravenous IgG Preparation (IVIG)

Synthetic human Aβ40 peptide (Calbiochem) was dissolved at 1 mg/mL in trifluoroacetic acid and diluted to 10 µg/mL with 0.1 M $NaHCO_3$—$Na_2CO_3$ buffer, pH 9.5. This solution was incubated with the wells of a NUNC Maxisorp F96 plate at 4° C. overnight (100 µL/well). The plate was then washed with washing buffer having 16 mS/cm conductivity or low conductivity concentration of NaCl. In both cases the washing buffer was 20 mM HEPES, 2 mM $CaCl_2$, 0.1% Tween 20 containing 0 (WBs) or 150 mM NaCl (WBi). The samples, a human reference plasma preparation #1R92 and an intravenous IVIG preparation (Gammagard Liquid, #LE12G036), were diluted using the respective washing buffer after addition of 10 mg/mL human serum albumin (hSA). These dilutions buffers were also used for blocking the plate, which was achieved by incubation at room temperature (RT) for 2 h. Then the plate was washed and afterwards incubated with the dilution series of the samples (100 µL/well) for 2 h. After a washing step, a rabbit anti-human IgG peroxidase conjugate (Dako P-214), diluted in the respective dilution buffer (1/1,000) was incubated with the plate (100 µl/well) at RT for 1 h. The incubation was terminated by a washing step and the bound peroxidase measured with the ready-to-use tetramethylbenzidin substrate SureBlue (KPL; 100 µL/well), incubated at RT until appropriate color developed. The reaction was then stopped with 100 µL/well of 1.5 M sulfuric acid. Within 60 min, the plate was then measured in an ELISA reader at 450 nm with a reference measurement at 620 nm. The optical densities (ODs) measured for the dilution series were then corrected by subtraction of a reagent blank, identical for all dilutions, and by subtraction of a sample- and dilution-specific blank. This specific blank was obtained by incubating the dilution series with blank wells, where no Aβ40 peptide has been coated. FIG. 1 shows the binding curves obtained for human plasma and the IVIG preparation using 16 mS/cm or low conductivity conditions throughout the whole assay.

The low conductivity conditions used during the assay clearly enhanced the binding of natural anti-Aβ IgG, present in human plasma and an IVIG preparation, to the plate-bound Aβ40 peptide. Thus, the signals obtained were at least 100-times higher when the low conductivity 20 mM-HEPES buffer was used throughout the whole assay for washing, diluting and detection. In addition, using an low conductivity buffer significantly (>50%) decreased the ratio between the signals measured on Aβ-coated and on blank wells. Binding to blank wells was reduced by more than 60% in the low conductivity system.

Example 2

Measurement of anti Aβ42 IgG in intermediates of IVIG

Eight lots of a process intermediate from the IVIG manufacturing process with a purity of higher than 85% were investigated for their anti-Aβ42 IgG levels using the methods described in Example 1. In contrast to the buffers described the buffers used did not contain $CaCl_2$. FIG. 2 shows the anti-Aβ42 IgG levels measured, expressed as blank-corrected OD per mg of IgG.

In all cases, the low conductivity conditions resulted in clearly increased signals. The assay signal obtained under low conductivity conditions was on average 50-times higher than that obtained under 16 mS/cm conditions. Individual increases ranged from 24 to 102 times. Concomitantly, the ratio between the signals on Aβ-coated and blank wells decrease by more than 50% on average and we found mean ratios of 0.13 and 0.04 for the 16 mS/cm or low conductivity conditions.

Example 3

Measurement of anti Aβ40 oligomer (CAPS) IgG in intermediates of IVIG

Plates were coated with anti-Aβ40 oligomers (CAPS, cross-linked β-amyloid protein species), obtained as described (O'Nuallain B. et al., (2010): J Clin Immunol May; 30 Suppl 1:S37-42). The assay was then done as described in Example 1 using buffers without $CaCl_2$. Eight lots of a process intermediate from the IVIG manufacturing process with a purity of higher than 85% were investigated for their anti-CAPS IgG levels. Table 2 shows the results giving the IgG concentrations (in µg/mL) and the corresponding signals obtained on the CAPS-coated (OD) and the blank wells (Blank). In addition, the ratio (Ratio) and the difference (Δ) between the corresponding signals and the signal normalized to the protein concentration, expressed as OD/mg are given:

TABLE 2

Measurement of anti-CAPS IgG

| Sample | IgG (µg/mL) | OD | Blank | Ratio | ΔOD | OD/mg |
|---|---|---|---|---|---|---|
| 16 mS/cm conditions | | | | | | |
| #001 | 654 | 1.107 | 0.075 | 0.07 | 1.033 | 1.58 |
| #002 | 421 | 1.086 | 0.095 | 0.09 | 0.991 | 2.36 |
| #003 | 595 | 1.418 | 0.189 | 0.13 | 1.229 | 2.07 |
| #004 | 493 | 1.324 | 0.112 | 0.08 | 1.212 | 2.46 |
| #005 | 456 | 1.133 | 0.100 | 0.09 | 1.034 | 2.27 |
| #006 | 487 | 0.917 | 0.160 | 0.17 | 0.757 | 1.55 |
| #007 | 398 | 1.061 | 0.174 | 0.16 | 0.887 | 2.23 |
| #008 | 515 | 0.802 | 0.133 | 0.17 | 0.669 | 1.30 |
| Low conductivity conditions | | | | | | |
| #001 | 6.54 | 0.489 | 0.009 | 0.02 | 0.480 | 73 |
| #002 | 4.21 | 0.424 | 0.014 | 0.03 | 0.410 | 98 |
| #003 | 5.95 | 0.601 | 0.005 | 0.01 | 0.596 | 100 |
| #004 | 4.93 | 0.437 | 0.009 | 0.02 | 0.428 | 87 |
| #005 | 4.56 | 0.529 | 0.004 | 0.01 | 0.525 | 115 |
| #006 | 4.87 | 0.596 | 0.012 | 0.02 | 0.584 | 120 |
| #007 | 3.98 | 0.579 | 0.021 | 0.04 | 0.558 | 140 |
| #008 | 5.15 | 0.471 | 0.011 | 0.02 | 0.460 | 89 |

The amount of antigen-antibody complexes formed increased as shown by the increased signal intensities obtained in the low conductivity assay system. This was observed for all samples investigated. The signal intensity increased on average 54-times with individual values between 35 and 77 times.

Example 4

Measurement of anti-Aβ Fibril IgG in Intermediates of IVIG

Plates were coated with anti-Aβ fibrils obtained as described (O'Nuallain B. et al., (2008). Biochemistry 47, 12254-12256). The assay was then done as described in Example 1 using buffers without $CaCl_2$. Eight lots of a process intermediate from the IVIG manufacturing process with a purity of higher than 85% were investigated for their anti-CAPS IgG levels. FIG. 3 shows the anti-Aβ fibril IgG levels measured, expressed as blank-corrected OD per mg of IgG.

The low conductivity conditions resulted in all cases in clearly increased signals. The assay signal obtained under low conductivity conditions was on average 64-times higher than that obtained under 16 mS/cm conditions. Individual increases ranged from 41 to 116 times.

Example 5

Measurement of Anti-DNA IgG in Human Plasma

Anti-DNA antibodies are well described human autoantibodies. Example 5 shows the binding curves obtained in a solid phase assay for anti-DNA IgG in human plasma obtained under low conductivity and 16 mS/cm assay conditions. Single stranded DNA (calf thymus, Sigma D8899) was incubated at 5 µg/mL with the wells of a NUNC Maxisorp F96 plate at 4° C. overnight (100 µL/well). The solid phase binding assay was then done as described in Example 1 using buffers without $CaCl_2$. The reference plasma preparation #1R01B00 from Technoclone (Vienna) was used. The dilution series started at a minimum dilution of 1/20 corresponding to an IgG concentration of 250 µg/mL. The assay layout, i.e. the method used for obtaining the sample- and dilution specific blank was done as described in Example 1. FIG. 4 shows the binding curves obtained using a log/lin form of presentation because of the huge differences in signal intensities observed for the two buffer systems.

The concentration-response curves clearly evidence that the low conductivity buffer increased the signal intensity at least by a factor of 100. In addition, the binding to blank wells which counted for 67% of the signal obtained under 16 mS/cm conditions, was decreased by 90% using the low conductivity conditions.

Example 6

Measurement of Anti-Tubulin IgG in Human Plasma

Tubulin is part of the microtubules, cylindrical filamentous structures present in all almost eukaryontic cells and part of the cytoskeletal system. Anti-tubulin autoantibodies are a normal component of some human sera, although the majority of anti-tubulin IgG seems to be present in form of immune complexes (Bernier-Valentin et al., (1988): *Clin. exp. Immunol.* 71, 261-268). Example 6 shows the binding curves obtained in a solid phase assay for anti-tubulin IgG in human plasma obtained under low conductivity and 16 mS/cm assay conditions. Tubulin (porcine, Sigma T6954) was incubated at 5 µg/mL with the wells of a NUNC Maxisorp F96 plate at 4° C. overnight (100 µL/well). The solid phase binding assay was then done as described in Example 1 using buffers without $CaCl_2$. The reference plasma preparation #1R01B00 from Technoclone (Vienna) was used. The dilution series started at a minimum dilution of 1/20 corresponding to an IgG concentration of 250 µg/mL. The assay layout, i.e. the method used for obtaining the sample- and dilution specific blank was done as described in Example 1. FIG. 5 shows the binding curves obtained using a log/lin form of presentation because of the huge differences in signal intensities observed for the two buffer systems.

The concentration-response curves clearly evidence that the low conductivity buffer increased the signal intensity at least by a factor of 100. In addition, the binding to blank wells, which counted for 50% of the signal obtained under 16 mS/cm conditions, was decreased by 90% using the low conductivity conditions.

Example 7

Measurement of Anti-Thyroglobulin IgG in Human Plasma

Example 7 shows the binding curves obtained in a solid phase assay for anti-thyroglobulin IgG in human plasma obtained under low conductivity and 16 mS/cm assay conditions. Thyroglobulin (porcine, Sigma T1126) was incubated at 5 µg/mL with the wells of a NUNC Maxisorp F96 plate at 4° C. overnight (100 µL/well). The solid phase binding assay was then done as described in Example 1 using buffers without $CaCl_2$. The reference plasma preparation #1R01B00 from Technoclone (Vienna) was used. The dilution series started at a minimum dilution of 1/20 corresponding to an IgG concentration of 250 µg/mL. The assay layout, i.e. the method used for obtaining the sample- and dilution specific blank was done as described in Example 1. FIG. 6 shows the binding curves obtained using a log/lin form of presentation because of the huge differences in signal intensities observed for the two buffer systems. The concentration-response curves clearly evidence that the low conductivity buffer increased the signal intensity at least by a factor of 100.

Example 8

Influence of Conductivity on the Sensitivity of the Detection of Autoantibody Anti-DNA IgGs from Human Plasma The conditions and DNA preparation described in Example 5 were also used to investigate the influence of the conductivity of the assay buffers used on the assay sensitivity. Thus, a 20 mM-HEPES buffer containing eight different concentrations of NaCl ranging from 0 to 150 mM was prepared and used as a washing buffer and after addition of 10 mg/mL hSA for diluting the human reference plasma sample. FIG. 7 shows the eight binding curves obtained.

A relationship between conductivity of the assay buffers and the sensitivity of the solid phase anti-DNA binding assay was apparent from the results. Thus, the IgG concentration required to obtain for example a blank-corrected signal of 0.2 differed by a factor of 1,000 when the signal obtained with the 150-mM NaCl buffer was compared with that of the buffer that did not contain NaCl. The inverse proportional relation between conductivity and signal intensity followed a mathematical function as shown in FIG. 8, where the relative signal intensities are plotted against the conductivity of the assay buffers used. The linear regression curve between conductivity and the logarithm of the signal intensity had a squared correlation coefficient of $R^2=0.98$, which strongly supports the conclusion that this increase in signal intensity is based on a functional relationship.

Example 9

Competition Study Showing the Specificity of the Binding of Anti-DNA and Anti-Tubulin IgG Under Low Conductivity Conditions Competition with soluble antigen is one common approach to demonstrate the specificity of binding tests using plate-bound antigen. This approach was therefore used to confirm that the low conductivity conditions did not favor non-specific binding, which was hypothesized as a possible explanation for the increased signal intensities observed under these conditions. This is shown in Example 9, where the binding of anti-DNA IgG and anti-tubulin to their plate-bound antigens was competed with soluble antigens. For that purpose, the plasma sample was incubated for 1 h with decreasing concentrations of the respective antigen. Then these samples were analyzed as described in Example 5 and Example 6, respectively. FIG. 9 shows the competition curves obtained with a clear concentration-dependent competition caused by the antigen in solution in both cases. Levels of 50% competition with the binding to the plate-bound antigen were obtained at concentrations of 9.9 an 18 µg/mL for DNA and tubulin, respectively. These data confirmed that the low conductivity of the assay buffers did not impact the specificity of the binding assays.

Example 10

Performance of a Conventional ELISA System Using Immunization-Derived Antibodies at Low Conductivity Assay Conditions Autoantibodies are present in the plasma without previous immunization or vaccination with their target antigen they are directed against. This is definitely not the case for nearly all antibodies used for ELISA, which are typically generated by active immunization with the target antigen. This process is mainly responsible for the differences between autoantibodies and their counterparts which are generated by active immunization. Example 10 investigates whether using low conductivity buffers for an ELISA assay of antibodies generated by active immunization increased the sensitivity in those instances. Thus, a well-established, validated ELISA for $\alpha_1$-antitrypsin based on using polyclonal rabbit IgG (Weber A. et al., (2011): Vox Sanguinis April; 100(3):285-97) exchanging the standard 16 mS/cm buffer with a low conductivity buffer system was used. The assay performed without any obvious changes. Contrary to the results of binding assays of various autoantibodies however, no increase in signal intensity was observed for the antibodies generated by active immunization.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Based on the present disclosure, those of skill in the art should appreciate that the present invention can be employed to detect autoantibodies spanning a range of different affinities, avidities, and reactivities (polyreactive vs. monovalent) and for different types of target antigens, including peptides and nucleic acids. It is contemplated that the methods provided herein can also detect autoantibodies having high avidity to target antigens which their $F_{ab}$ regions are specific for though not necessarily with enhanced sensitivity over conventional ELISA assays.

What is claimed is:

1. A method for detecting an autoantibody in a biological sample, said autoantibody being specific for a target antigen, the method comprising the steps of:
    (a) contacting the biological sample under a low conductivity condition with the target antigen for which the autoantibody has specific binding affinity; and
    (b) detecting the binding of said target antigen to said autoantibody in the biological sample,
    wherein said target antigen is immobilized on a solid phase and the presence of said binding is indicative of the autoantibody in the biological sample, and
    wherein the low conductivity condition has a conductivity of less than the conductivity of a 90 mM sodium chloride solution.

2. The method of claim 1, wherein the autoantibody is a non-affinity maturated autoantibody.

3. The method of claim 1, wherein the biological sample is selected from the group consisting of blood, serum, plasma, a fraction thereof, and a processed derivative thereof.

4. The method of claim 1, wherein the biological sample is an intravenous IgG preparation.

5. The method of claim 1, wherein the biological sample is derived from a human.

6. The method of claim 1, wherein the low conductivity condition has a conductivity of less than the conductivity of a 60 mM sodium chloride solution.

7. The method of claim 1, wherein the low conductivity condition has a conductivity of less than the conductivity of a 40 mM sodium chloride solution.

8. The method of claim 1, wherein the low conductivity condition has a conductivity of less than the conductivity of a 20 mM sodium chloride solution.

9. The method of claim 1, wherein the solid phase comprises a microplate.

10. The method of claim 1, wherein said detection step (b) comprises:
    (i) contacting the biological sample with a species-specific antibody which binds to the autoantibody against the target antigen under conditions sufficient for specific binding of the species-specific antibody to the corresponding autoantibody; and
    (ii) detecting any complex comprising the target antigen, the autoantibody, and the species-specific antibody.

11. The method of claim 10, wherein the species-specific antibody is conjugated to a detectable moiety.

12. The method of claim 11, wherein the detectable moiety comprises a direct label.

13. The method of claim 12, wherein the direct label comprises peroxidase.

14. The method of claim 11, wherein the detectable moiety comprises an indirect label.

15. The method of claim 11, wherein the (ii) detecting any complex comprises contacting the detectable moiety with an indicator reagent.

16. The method of claim 1, wherein the autoantibody is selected from an IgG antibody, an IgA antibody, and an IgM antibody.

17. The method of claim 1, wherein the biological sample is diluted at least 1,000-fold with a low conductivity dilution buffer prior to step (a).

18. The method of claim 17, wherein the low conductivity dilution buffer has a conductivity of less than the conductivity of a 90 mM sodium chloride solution.

19. The method of claim 1, further comprising, prior to step (b): washing the solid phase with a low conductivity wash buffer.

20. The method of claim 19, wherein the low conductivity wash buffer has a conductivity of less than the conductivity of a 90 mM sodium chloride solution.

21. The method of claim 1, wherein the autoantibody is selected from the group consisting of an amyloid-β-specific autoantibody, a DNA-specific autoantibody, a tubulin-specific autoantibody, and a thyroglobulin-specific autoantibody.

22. The method of claim 1, wherein the autoantibody is an amyloid-β-specific autoantibody and the target antigen is an amyloid-β antigen in a form selected from an amyloid-β monomer, amyloid-β dimer, amyloid-β oligomer, a crosslinked amyloid-β oligomer, and amyloid-β fibril.

23. The method of claim 1, wherein the autoantibody is a DNA-specific autoantibody and the target antigen is a single-stranded DNA or a double-stranded DNA.

24. The method of claim 17, wherein the low conductivity dilution buffer has a conductivity of less than the conductivity of a 60 mM sodium chloride solution.

25. The method of claim 17, wherein the low conductivity dilution buffer has a conductivity of less than the conductivity of a 40 mM sodium chloride solution.

26. The method of claim 17, wherein the low conductivity dilution buffer has a conductivity of less than the conductivity of a 20 mM sodium chloride solution.

* * * * *